US010055547B2

(12) United States Patent
Chari et al.

(10) Patent No.: US 10,055,547 B2
(45) Date of Patent: Aug. 21, 2018

(54) INTERMEDIATE CHECK POINTS IN MEDICAL CARE LINES FOR AUTOMATICALLY IDENTIFYING CARE DEFICIENCIES

(71) Applicant: HCA Holdings, Inc., Nashville, TN (US)

(72) Inventors: Ravi S. Chari, Nashville, TN (US); Jenny F. Barber, Franklin, TN (US); Dawn A. Winans, Brentwood, TN (US)

(73) Assignee: HCA Holdings, Inc., Nashville, TN (US)

( * ) Notice: Subject to any disclaimer, the term of this patent is extended or adjusted under 35 U.S.C. 154(b) by 0 days.

(21) Appl. No.: 14/304,604

(22) Filed: Jun. 13, 2014

(65) Prior Publication Data
US 2014/0372138 A1 Dec. 18, 2014

Related U.S. Application Data

(60) Provisional application No. 61/835,139, filed on Jun. 14, 2013.

(51) Int. Cl.
G06F 19/00 (2018.01)
G16H 40/20 (2018.01)

(52) U.S. Cl.
CPC .......... *G06F 19/327* (2013.01); *G16H 40/20* (2018.01)

(58) Field of Classification Search
CPC ........ G06Q 50/22; G06Q 50/24; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00
See application file for complete search history.

(56) References Cited

U.S. PATENT DOCUMENTS

| | | | |
|---|---|---|---|
| 2002/0032583 A1* | 3/2002 | Joao | G06F 19/322 705/2 |
| 2009/0125348 A1* | 5/2009 | Rastogi | G06Q 30/018 705/7.32 |
| 2012/0078656 A1* | 3/2012 | Wennberg | G06F 19/328 705/2 |

OTHER PUBLICATIONS

Author Unknown, "About Crimson Continuum of Care", The Advisory Board Company, retrieved from http://www.advisory.com/technology/crimson-continuum-of-care/about-crimson-continuum-of-care on Jul. 7, 2014, 2 pages.

* cited by examiner

*Primary Examiner* — Sean K Hunter
(74) *Attorney, Agent, or Firm* — Kilpatrick Townsend & Stockton, LLP

(57) ABSTRACT

A quality of medical care can be estimated based on factors such as a mortality rate or complications rate. However, by this point, poor care may have already reached its consequence. In some embodiments, characteristics pertaining to a care experience are analyzed to identify those predictive of a health result. The identified characteristics may include ones that depend on care factors, such that they are not, alone, easy to manipulate. Those characteristics can then be monitored, and unsatisfactory characteristics can be addressed.

20 Claims, 16 Drawing Sheets

FIG. 15

INTERMEDIATE CHECK POINTS IN MEDICAL CARE LINES FOR AUTOMATICALLY IDENTIFYING CARE DEFICIENCIES

CROSS-REFERENCE TO RELATED APPLICATIONS

This application claims the benefit of and priority to U.S. Provisional Application No. 61/835,139, filed on Jun. 14, 2013, which is hereby incorporated by reference in its entirety for all purposes.

BACKGROUND

This disclosure relates in general to methods and systems for identifying and utilizing check points during medical care (e.g., to automatically predict other care-quality metrics and/or to offer care improvement plans).

Medical institutions provide medical care to a large number of people. Even for a particular type of care, the care may include many different elements, many of which may be performed by different actors. Poor medical care has serious consequences, and can unfortunately even lead to unnecessary death. However, identifying care problems can be difficult. Results such as death and maintained illness can occur even without poor medical care, such that parties can be reluctant to blame medical care for such a result. Further, as noted, medical care includes many elements. Patients, care providers and supervisors may be unaware of all of the care elements and can be oblivious to particular reasons for concern pertaining to specific elements. Thus, a party can have difficulty attributing a negative consequence to a particular care element. Finally, even if a negative health consequence is attributed to a care element, the seemingly avoidable health consequence would have already occurred.

SUMMARY

In one embodiment, the present disclosure provides a method and system for tracking medical-care results and identifying check points within the medical care where assessments can be made that are indicative of a quality of care. Specifically, data are aggregated across a set of patients having received a type of care. Care results (e.g., mortality, complications, length of stay at a hospital, etc.) are tracked and are analyzed with respect to a set of potential check-point indicators. The potential check-point indicators can include variables which themselves are results of care actions; for example, the potential indicators can include surgery durations, strengths of post-surgery pain medication taken by patients, a post-surgery patient-reported nausea rating, post-procedure platelet counts, administration of an appropriate medication (or dosage), appropriate timing of medication administration, etc.

A subset of check-point indicators is determined to be predictive of one or more care results. This determination can account for the fact that care results are not to be analyzed in isolation (e.g., not wanting to prioritize short hospital stays if the consequence is increased readmissions). For each check-point indicator, a goal is set, which can include a value or range of values that correlates with positive care results. In some instances, the goal is relative, such as a goal directed to improving a performance within an institution or performing comparably to other institutions providing similar care.

Once check-point indicators are identified (e.g., for a particular care line, which can relate to a patient condition, treatment type, surgery type, etc.), the check-point indicators can then be automatically monitored. The monitoring can occur promptly and/or in real-time, such that (for example) case data (e.g., medical-record data, patient notes and/or medical-equipment outputs) is processed within days, hours, minutes or even seconds from time of receipt and/or such that check-point indicators (e.g., associated with each working entity, patient or patient group) are updated at least once a week, day, hour, minute or ten seconds.

In one instance, multiple check-point indicators are identified to correspond to a care line. A combination function can be used to combine the check-point indicators to produce an overall score for the care line. In one instance, each check-point indicator is first assessed (e.g., to determine whether and/or where it falls within an acceptable range, to determine whether a change of the indicator is acceptable, to determine an extent to which it exceeds a value, etc.) to produce a processed indicator value. Multiple processed indicator values can be weighted and combined to produce a care score (or net care result).

Each of one, more or all check-point indicators and/or a care score can be generated for a variety of entities and/or levels (e.g., at a region, institution, department, physician group, physician or patient group level). Each of one, more or all check-point indicators and/or a care score can be evaluated based on a goal and/or criterion, which can depend on (for example), comparing absolute values to a threshold, comparing values to individual or aggregated values corresponding other entities and/or levels, comparing changes in values (or a second derivative of values) to a threshold, etc. A report can reflect individual check-point indicators, an evaluation of individual check-point indictors, a care score and/or an evaluation of a care score. In one instance, a report is routinely generated, transmitted and/or presented. In one instance, a report is generated upon request. The report can allow a reviewer to quickly assess an overall performance of a care line and to further identify one or more particular check points with sub-optimal performance.

In one instance, if a performance criterion (for a check-point indicator or care score) is not satisfied, an alert and/or a proposed action plan can be presented or transmitted. For example, if it is determined that an above-threshold percentage of patients are not receiving a recommended medication, a plan can include requiring a supervisor to follow-up with a group of patients within a time period in which the medication is to be received. As another example, if it is determined that an increasing number of patients are reported as having a post-operative infectious complication, a plan can include increasing frequency of using particular sterility procedures.

In some embodiments, systems and/or methods can be provided for providing presentations to monitor a quality of care being provided to patients. A case data store that includes a plurality of cases is accessed. Each case of the plurality of cases identifies a patient, a type of a medical care received by the patient, an entity (e.g., hospital, physician, nurse, technician or team of medical professionals) that provided the medical care, a set of check-point indicators, and a care result variable. Each check-point indicator of the set of potential check-point indicators characterizes a feature of the medical care received by the patient (e.g., an operation performed, treatment administered, medication administered, medical test provided, duration of an operation, etc.) or a health characteristic of the patient during a provision of the medical care (e.g., a condition stage, a vital sign, a subjective pain level, etc.). The care result variable identifies whether an event occurred after or during the provision of the medical care, the event relating to the patient's health and being indicative of a quality of the medical care. For example, the care result variable could indication whether the patient experienced a complication, was readmitted, whether an existing condition improved, and/or a length of stay at a hospital.

A first set of cases is identified from amongst the plurality of cases. Each case of the first set of cases is associated with a same type of medical care (e.g., a same care line), a same entity and medical care occurring at least partly within a first time period. A second set of cases is identified from amongst the plurality of cases. Each case of the second set of cases is associated with the same type of medical care, the entity and medical care occurring at least partly within a second time period.

For each set of the first set of cases and the second set of cases, a population care-result statistic is generated that corresponds to the time period for the set based on the care-result variable in at least some of the set of cases. For each set of the first set of cases and the second set of cases, a set of population check-point statistics is generated that corresponds to the time period for the set. Each population check-point statistic in the set of check-point statistics is based on a check-point indicator in the set of check-point indicators in at least some of the set of cases.

A first presentation that includes the population care-result statistic and the set of population check-point statistics for the first set of cases is presented. A second presentation is presented that includes the population care-result statistic and the set of population check-point statistics for the second set of cases.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures:

Figure 15:
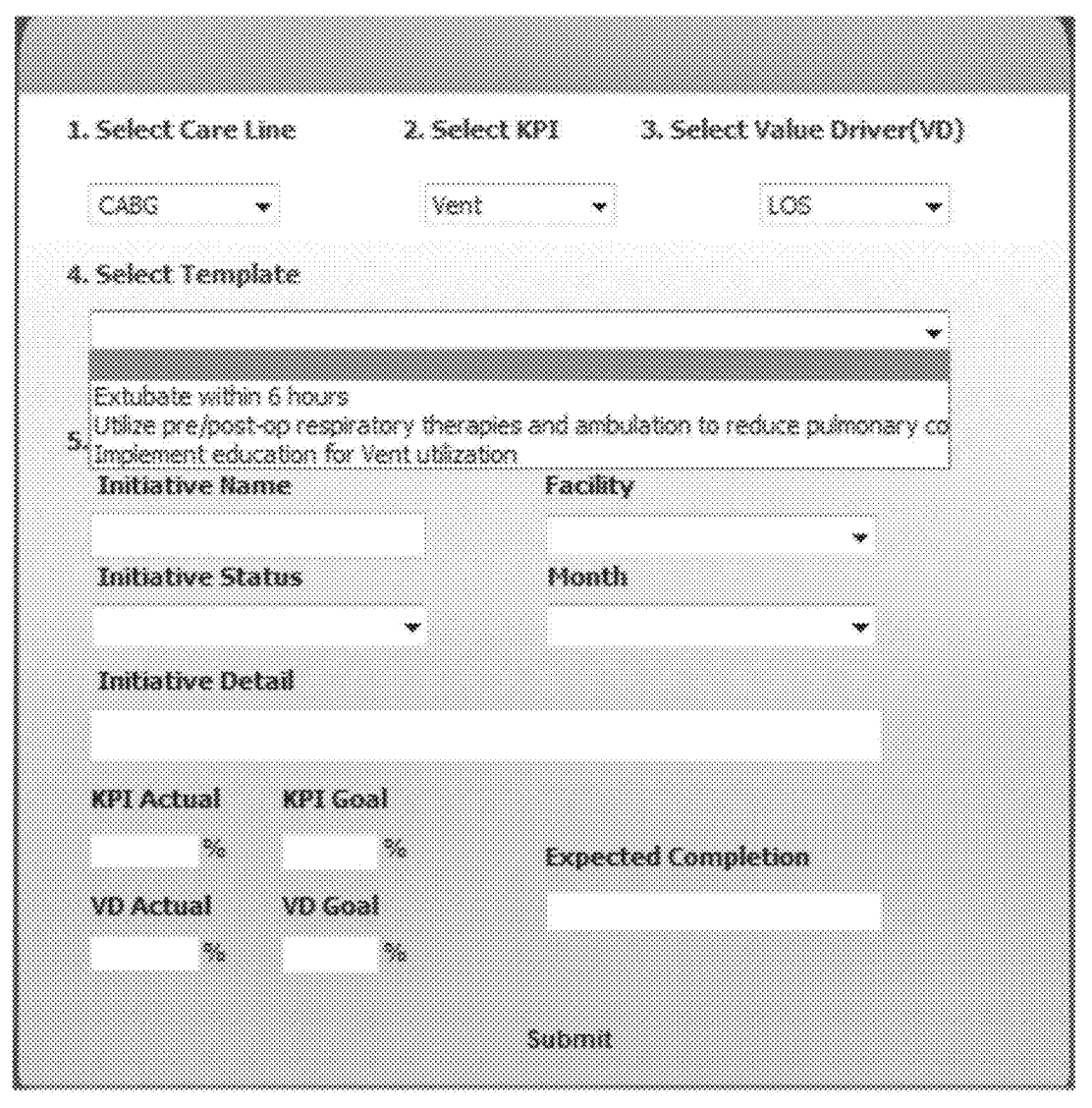

FIGS. 11-16 each show at least a portion of an interactive presentation for reviewing care data and/or specifying presentation characteristics and/or care recommendations.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes can be made in the function and arrangement of elements without departing from the spirit and scope as set forth in the appended claims.

Figure 1:
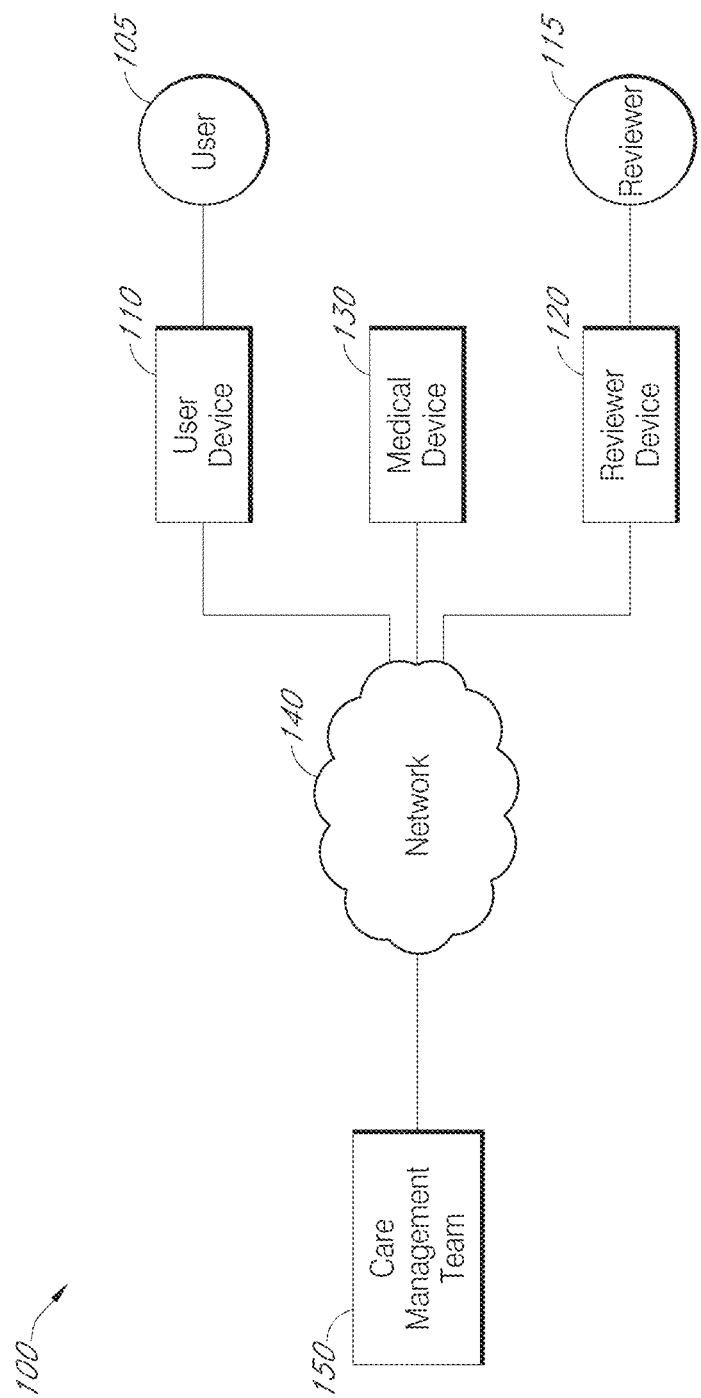
FIG. 1 depicts a block diagram of an embodiment of a medical-care interaction system.

Referring first to FIG. 1, a block diagram of an embodiment of a medical-care interaction system 100 is shown. Users 105 and reviewers 115 can interact with a care management system 150 via respective devices 110 and 120 and a network 140, such as the Internet, a wide area network (WAN), local area network (LAN) 114 or other backbone. Further, medical devices 130 can provide or receive data from care management system 150 from a same or different network 140. In some embodiments, care management system 150 is made available to one or more of users 105 and/or reviewers 115 via an app (that can be downloaded to and executed on a portable electronic device) or a website. It will be understood that, although only one user 105, user device 110, reviewer 115, reviewer device and medical device 130 are shown, system 100 can include multiple users 105, user devices 110, reviewers 115, reviewer devices and/or medical devices 130.

Users 105 can include parties with access to pre-, intra-, or post-care medical data, such as recent medical records, current vital signs, current procedure characteristics, etc. These users 105 can be parties collecting such data or parties who receive the data after it has been collected. Examples of users 105 include care providers (e.g., physicians, nurses, surgeons, assistants), and medical-institution administrators. Reviewers 115 can include parties with access to high-level care information and/or with the ability to institute changes in the provision of care. For example, reviewers 115 can include supervisors, board directors, managers, and institution operators. In some instances, a reviewer 115 can also be a user 105. For example, a physician may both be able to enter data about his patients and view reports pertaining to his performance. Reviewers 115 can include parties within an institution at issue (e.g., a chief medical operator or hospital CEO) or outside of the institution (e.g., being associated with an insurance company or accreditation counsels).

Reviewers 115 can have unlimited or limited reviewing access. For example, a reviewer 115 can be allowed to access data or reports for particular levels or entities. For example, for a reviewer 115 can be granted selective access to access performance indicators and care scores for a care line in a single hospital and for all personnel involved with the care line. In some instances, a reviewer 115 can be granted access to view anonymized data (e.g., for all or select levels and/or entities), which can aid reviewer 115 in, e.g., comparing data.

Users 105 can enter input to care management system 150 pertaining to medical care. As will be described in further detail below, user 105 can cause a case to be generated or updated to include care-independent case characteristics (e.g., a patient's ailments, past procedures, current medications, weight, etc.), care characteristics (e.g., pre-operation preparations, type of procedure performed, procedure time duration, length of stay within a ward or unit, etc.), and/or care-result characteristic (e.g., any readmission, complication, death, etc.). In some instances, medical data (which can include care characteristics) is provided by medical devices 130. Medical devices 130 can be programmed to periodically, routine or continuously collect medical data from a patient. In some instances, medical devices 130 themselves identify the patient associated with the data (e.g., based on prior user entries into the device). In some instances, a user 105 identifies via user device 110 that a medical device 130 is or will be collecting data from a particular patient. Medical data can be pushed from medical device 130, or care management system 150 can pull such data.

In some instances, some or all input received by users 105 and/or medical devices 130 can be locally stored at user devices 110 and/or medical devices 130 and/or stored at an intermediate system and can be periodically or routinely uploaded to care management system 150. For example, upload can occur at routine time intervals, upon receiving a threshold quantity of data, upon receiving an instruction from a user 105 to upload the data, etc.

Care management system 150 can use population data to identify one or more check-point indicators correlated with care results and to identify recommended values for the indicators. The check-point indicators can correspond to or be care characteristics entered by users 105. Each check-point indicator can be estimated to be influenced by one or more controllable parameters (e.g., preparatory pre-procedure tests performed, patient education provided, a number of procedures performed by a physician within a time interval, etc.).

Values of the indicators can be monitored. The values can be summarized, for example, for a particular institution, actor, time period, procedure type and/or patient group. The summarized values and/or values for particular cases can be presented to a reviewer 115. If, for a given check-point indicator, the values for a specific case or for a population do not meet the recommended value(s), an alert can be generated and presented to reviewer 115 and information about controllable parameters that influence the check-point indicator can also be presented.

User device 110, reviewer device 120 and/or medical device 130 can each be a single electronic device, such as a hand-held electronic device (e.g., a smartphone). It will be understood that user device 110, reviewer device 120 and/or medical device 130 can also include a system that includes multiple devices and/or components. The device(s) 110, 120 and/or 130 can include a computer, such as the desktop computer, a laptop computer or a tablet. Medical device 130 can include a monitor, such as a heart-rate monitor, oxygen monitor, blood-pressure monitor, etc. In some instances, a party 105 and/or 115 uses different devices at different times to interact with care management system 150. For example, user 105 can use a tablet to enter a patient's care-independent characteristics and can subsequently use a smartphone to enter intra-care characteristics.

Figure 2:
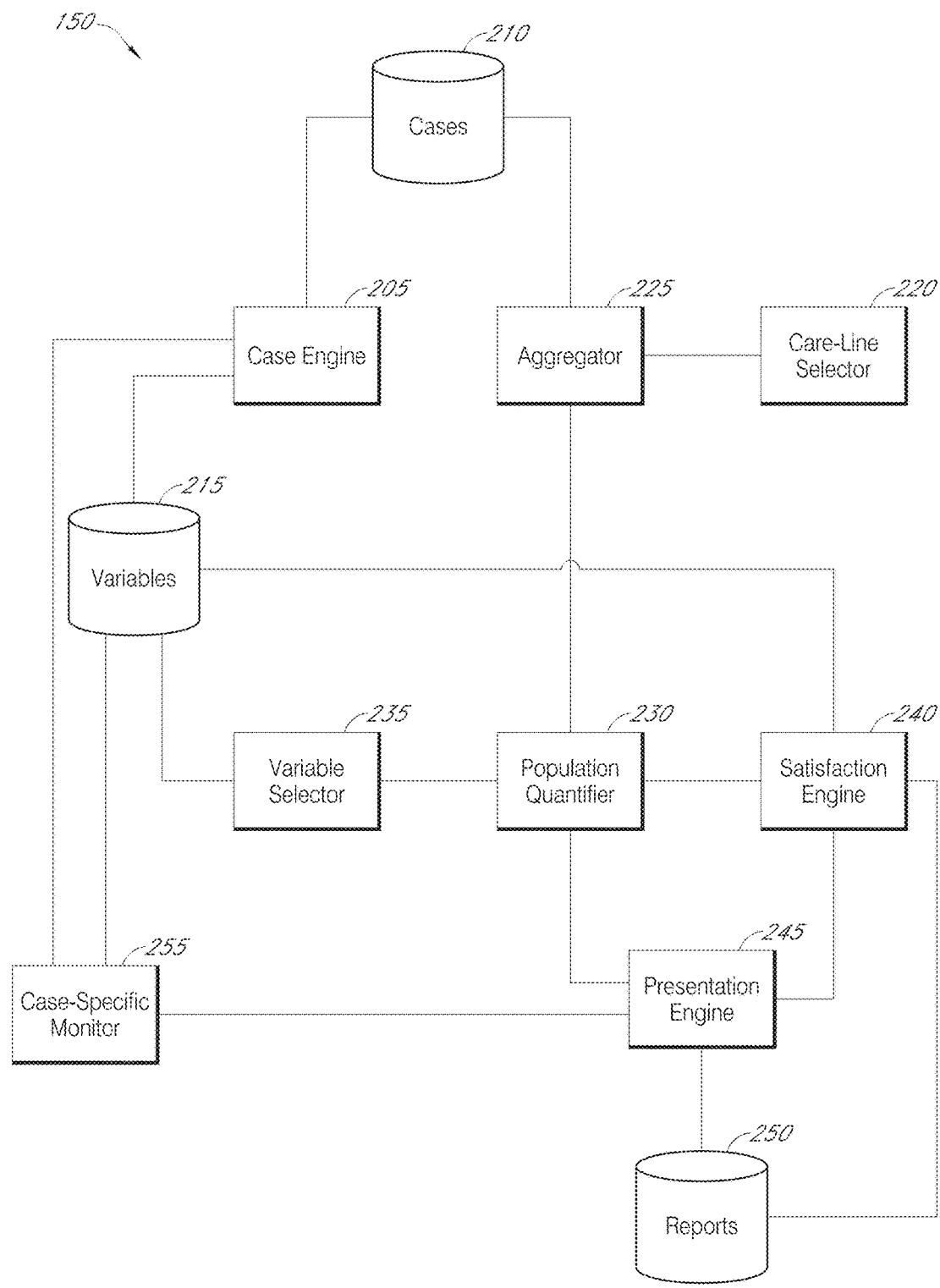
FIG. 2 depicts a block diagram of an embodiment of care management system.

Referring next to FIG. 2, a block diagram of an embodiment of care management system 150 is shown. Care management system 150 can be, in part or in its entirety, in a cloud. In some instances, at least part of care management system 150 is present on a device, such as a user device 110 and/or reviewer device 120. For example, a case engine 205 can be on user device 105, a presentation engine 245 can be on a reviewer device 120, and population quantifier 230 can be in a cloud. In some instances, part of a component (e.g., part of presentation engine 245 or population quantifier 230) resides in a cloud and another part of the component resides in a device. Thus, care management system 150 can include a distributed system.

Care management system 150 includes a case engine 205, which generates and updates cases. Each case can correspond to a patient and/or a particular instance of care (e.g., a surgery). The cases are stored in a case data store 210. A case can be generated upon, for example, receiving an indication that a patient has been schedule for care, has been admitted to an institution, has arrived at an institution for care and/or has begun to receive care. A case can include information (which can include data) sent from a data-collecting medical device 130. The case can further or alternatively include information (which can include data) received from a user device 110, the information having been entered into device 110 by a user 105 (e.g., in response to collecting medical data, receiving written or oral query responses from patient, characterizing a situation or receiving hand-written records). As described further below, a case can include care-independent case characteristics, care characteristics and/or care-result characteristics. A variables data store 215 can define which characteristics must or can be collected for case generation or at later time periods (e.g., following a scheduled procedure).

A case can include care-independent case characteristics, such as a patient's identifying information (e.g., name, social-security number, demographic characteristics (e.g., age, race, sex), physical characteristics (e.g., height, weight), correspondence information (e.g., home address, telephone number, email address), billing information (e.g., billing address, insurance company, insurance member ID), and/or general medical information (e.g., identifications of past surgeries, previous diagnoses, current symptoms, current medications, allergies, family medical history, primary physician).

A case can include care characteristics, which can include detail a type of care (e.g., identification of a care line, such as a line for acute myocardial infarction response, hip replacement, knee replacement, spinal surgery, sepsis response, coronary artery bypass grafting, or stroke response), features of the care provision (date(s) of the care, physicians/nurses providing care, an institution providing care), care details (e.g., a surgery duration, anesthesia used, blood loss, incision length, type of hip or knee replacement, which medications were administered, a time of medication administration, a dosage of medication administration, etc.), the preparation provided for a procedure and/or care provided following a procedure. For example, if a patient is to receive a surgery, the preparation can include: providing education to the patient about how to facilitate rehabilitation, hydrating the patient and/or performing screens to localize areas of interest (e.g., a clot). Recovery for the care can include replacing bandages, routine visual monitoring for signs of infection, providing pain medication, and providing rehabilitory-exercise training Pre-care and/or post-care characteristics can identify any respective efforts provided, dates of such provision and/or individuals providing the preparation.

Care characteristics can also or alternatively characterize the patient during periods immediately preceding, during or immediately following the care. For example, a care characteristic can include a patient's (instantaneous or time-averaged) blood pressure, temperature, heart rate, pulse rate, oxygen level, or subjective pain level.

A case can include a care-result characteristic, which identifies and characterizes any health events following the care provision that may be attributable to the care. Such events can include, e.g., a death, complication (e.g., infection or blood clot following a surgery), readmission to a same or different hospital, length of stay at an institution, hospital-acquired condition, and/or cost of providing care (and/or post- and/or pre-care). Any such event can be accompanied by an indication as to whether it is likely that the event was attributable to the care. For example, a post-care death can be identified as being due to a vehicular accident such that it can be determined that care improvements would likely have been un-influential in the death.

Information in a case can be gradually built based on various inputs from users 105 and/or data from medical devices 130. In some instances, case engine 205 generates and presents forms to users 105 to collect pertinent information and/or pulls data from medical devices 130. Cases can include a standard format. Case data store 210 can be secured such that, for example, cases can be edited only in response to authorized events (e.g., receiving uploads from a secure channel or receiving inputs from an authorized user 105) and/or can only be released for access to authorized reviewers 115.

Cases can pertain to different types of care, such as different procedures (e.g., hip, back or knee surgery), different responses (e.g., responses to a heart attack, stroke or sepsis) or other medical events (e.g., childbirth, poison treatment, or abrasion/gun-shot repair). Care can then be evaluated and improved in a care-specific manner.

A care-line selector 220 can identify a type of care (i.e., a care-line) of interest. The care-line can be identified based on input from a reviewer 115. In some instances, care lines are selected in a routine manner (e.g., to analyze and/or improve care of each line).

Once care-line selector 220 has selected a care-line, an aggregator 225 accesses case data store 210 and identifies a set of cases pertaining to the selected care-line. Additional restrictions can be imposed to, e.g., require that the cases be ones identifying medical care having been provided within a specified time period, performed at a specified institution, performed for a specified patient group (e.g., within an age range without other health conditions).

The aggregated cases can then be analyzed by a population quantifier 230. In some instances, population quantifier 230 determines relationships between variables. For example, population quantifier 230 can identify care characteristics correlated with one or more care results (e.g., a lack of negative care results). This analysis can involve considering a plurality of care results (e.g., mortality, occurrence of complications, contraction of hospital-acquired conditions, readmission to an institution, cost of care, and/or length of admission). The care results can be results that occur during care (e.g., a surgery complication) of subsequent to care (e.g., a readmission). The care results can be numeric (e.g., identifying a number of days of a hospital stay or a severity of a complication) or binary (e.g., identifying that "No" complications occurred). A simplistic correlation can be inadequate to capture whether a particular characteristic is predictive of a net positive care result. Population quantifier 230 can thus employ multi-dimensional correlation techniques, modeling techniques and/or multi-dimension statistical techniques. The analysis can further account for intervening variables that are not a consequence of any care but can also influence a health result. For example, older patients can be more likely to experience care complications.

In some instances, the analysis includes determining (e.g., for each case) a net care-result metric or score determined based on multiple care results. The metric determination can include weighting, step-functions and/or normalizing. For example, a metric can begin as being equal to 1, can be decreased for any complication (e.g., by an amount depending on a severity), can be set equal to zero if a patient died, and normalized based on a patient's age. The metric can then be used as a dependent variable to determine which characteristics are most predictive of a strong metric.

Based on the analysis, a variable selector 235 can select a subset of characteristics to monitor during care, which can be identified as being check-point indicators. Same or different check-point indicators can apply to assess an individual case as compared to an assessment of a group of cases (e.g., all relating to an institution or physician). The subset can include one or more characteristics that are correlated with a positive individual or combined care result. Exemplary check-point indicators include when an antibiotic was discontinued, a regularity of antibiotic administration, appropriate selection of an antibiotic, whether and/or an extent to which atrial fibrillation occurred, whether a ventilator was used, a consistency and/or an extent to which blood glucose is managed, whether and which blood products were used, and whether a Foley catheter was timely and appropriately removed.

Variable selector 235 can select characteristics by analyzing significance values, correlation strengths, model weights and/or data availability. Variable selector 235 can identify a set number of characteristics (e.g., a two characteristics most predictive of an overall care-result metric) or a flexible number of characteristics (e.g., all characteristics having an assigned weight in a model above a threshold). This identification can include weighting the identified check-point indicators, where high weightings can indicate that undesired values of the indicator are strongly correlated with negative care results and/or are correlated with dramatic negative care results. The categorization of a particular characteristic being a check-point indicator and/or any weight with the indicator can be expressed in variables data store 215.

In some instances, at least some of the selected characteristic(s) can be ones which themselves are results of care provision and not easily individually controlled. For example, a surgery duration can be a result of a surgeon's skill, a surgeon's workload, amount of human assistance during the surgery, pre-surgery scans to understand the surgical area, etc. Despite these dependencies, a surgery duration can be indicative as to whether optimal care during and before the surgery was provided. The selected characteristic(s) can also or alternatively be ones which are too pre-mature to be classified as care results. Instead, the characteristics can be ones measurable or observable during care provision (e.g., during a procedure or immediately following the procedure). In some instances, at least some of the selected characteristic(s) can be ones which can be easily individually controlled. For example, a characteristic can include medication administration, a frequency of checking a vital sign, a shift duration of a medical professional and/or a number and/or experience of medical professionals working.

In addition to selecting the check-point indicators to monitor, variable selector 235 can identify a recommended value or range of values for each indicator. These value(s) can be defined as part of an indicator satisfaction criterion. An indicator satisfaction criterion can be set to be one which is empirically associated with one or more absolute or relative positive care results. In some instances, such association is balanced with practicality and/or cost. For example, a correlation analysis can indicate that optimal post-spinal-surgery care results occur following spinal surgeries lasting less than 30 minutes. However, it may be recognized that it would be difficult to impossible to consistently achieve such short surgery durations, so a surgery-duration check-point indicator can be associated with an 'under-120-minutes satisfaction criterion. An indicator satisfaction criterion can be absolutely set (e.g., based on modeling or correlation analyses), set as one which would indicate that a particular entity (e.g., institution, physician, surgery team, etc.) is improving in providing care (over time), or set as one which would indicate that a particular entity is providing care at a specific level (e.g., within a top 70%) relative to other entities. Variable selector 235 can store the indicator satisfaction criteria in variables data store 215. Satisfaction criteria can be the same for population and case-specific analyses or they can differ. For example, as individual case characteristics may be noisier than population case characteristics, population criteria can be more stringent than case-specific criteria.

Population quantifier 230 can also identify one or more controllable parameters associated with a check-point indicator underlying a population statistic. This identification can be performed once or multiple times (e.g., at routine intervals, upon identifying a check-point indicator not passing a satisfaction criterion, etc.). The associations can be stored in variables data store 215. The associations can also be global or non-global (e.g., applying to specific institutions and/or care-lines).

The controllable parameters can be ones thought to be directly controllable by users or other actors in an institution and ones that influence one or more check-point indicators. In some instances, a controllable parameter is directly related to a check-point indicator (e.g., a frequency of monitoring a patient's blood pressure may be both a controllable parameter and a check-point indicator); in some instances, they are different (e.g., changing requisite pharmacy approval of medication dispersal may be a controllable parameter related to administration of an appropriate medication). Exemplary controllable parameters can include changing a timing, frequency or type of monitoring; changing a number of actors interacting with a patient (e.g., reducing nurse changes or increasing nurse changes to allow shorter shifts); changing oversight on medication use; changing a type, timing or frequency of education provided to a patient; changing a type, timing of frequency of education provided to a physician or nurse; or changing a management structure in charge of part or all of a care line. Multiple controllable parameters can be associated with a single check-point indicator and/or a single controllable parameter can be associated with multiple check-point indicators.

A controllable parameter can be associated with a check-point indicator based on manual user input or based on an automatic population analysis. For example, cases can identify parameter values and indicator values, and population quantifier 230 can then identify which parameters influence which check-point indicators. As another example, a user can identify parameter values in effect for particular periods of time at an institution. Population quantifier 230 can then assess how check-point indicators for cases with an event (e.g., admission, pre-procedure, procedure or post-procedure) in one period of time compare to check-point indicators for cases with an event in another period of time. For example, population quantifier 230 can associate each case with a parameter value (based on a case event time) and can then use a correlation or modeling technique to identify influential parameters.

It will be appreciated that an identity of a check-point indicator, a satisfaction criterion, and/or a controllable-parameter association can be globally determined or can be separately determined for population analyses and for case-specific analyses. The latter approach can, e.g., set satisfaction criteria that recognize that a high value may be within an appropriate noise variation for case-specific analyses but that the same value, if it is common throughout an entire population is reason for concern. Further, the latter approach can benefit from a reality that case-specific monitoring more often provides for an opportunity for measures to be taken to "fix" a concerning indicator and not let it lead to a negative care result. Thus, e.g., a check-point indicator can have a first controllable-parameter association for a population-analysis instance and a second association for a case-specific instance. For example, supposing that an indicator characterizes an amount of pain medication requested by patients. If this is too high on a population level, it may be advantageous to consider changing incision techniques. If the indicator is high for a particular case, is may be advantageous to take precautions against narcotic addiction.

It will further be appreciated that an identity of a check-point indicator, a satisfaction criterion, and/or a controllable-parameter association can be globally determined or can vary across levels and/or entities. For example, a surgery duration of under 120 minutes may be associated with positive care results at a first hospital, while a surgery duration of under 180 minutes may be associated with positive care results at a second hospital.

In addition to identifying check-point indicators and controllable-parameter associations based on empirical analyses, population quantifier 230 can also monitor indicators at a population level. Specifically, aggregator 225 can repeatedly collect cases, which can (in some instances) include newer cases for which care is not yet complete and/or insufficient opportunity to assess any care results. Each collection can pertain to a different time period. For example, the collection may always include cases for which a surgery or other procedure was performed within the last 30 days or for which a patient was released from an institution within the last 3 months. In some instances, aggregator 225 collects cases for different or sequential (e.g., non-overlapping) time periods. For example, a first group could include cases having a surgery within the last 30 days, a second group could include cases having a surgery within the last 60-30 days, etc. Again, the aggregation can include other restrictions, such as requiring a procedure (e.g., surgery) to have been provided by a specified institution.

Aggregation can also or alternatively be performed according to reviewer input. For example, a reviewer 115 can request a report or population statistic pertaining to a particular care line, a particular institution, a particular physician (e.g., surgeon) and/or a particular time period (e.g., during which a procedure was performed or a patient was discharged). Aggregator 225 can then aggregate the cases accordingly.

Population quantifier 230 can, in some instances, generate a population statistic characterizing each, one, some or all check-point indicators. The statistic can include a mean, median, mode, range, maximum, minimum, variance, etc. The statistic can include a normalized or un-normalized score where, e.g., a maximum score would indicate optimal or acceptable check-point values. The statistic can include a comparative statistic, such as one expressing a change in an absolute indicator statistic relative to a comparable absolute indicator statistic from a past time period or relative to a comparable absolute indicator statistic from other institutions. A comparative statistic can include a percentage, ranking or binary indicator (e.g., indicating improvement/ worsening relative to an older comparable statistic). For example, population quantifier 230 can determine that, for a particular check-point indicator, an average value for cases pertaining to having a procedure in the last month was 30% higher than an average value for cases having a procedure two months ago, 25% lower than a minimum value set forth in a satisfaction indicator, and better than 10% of comparable indicators from other institutions.

A satisfaction engine 240 can assess the population statistic in view of one or more satisfaction criteria (stored in variables data store 215). A result of the assessment can be identified as a satisfaction result, which can include a score. A scale for the score can be binary, non-binary, discrete or continuous. The scale can be bounded or unbounded. The scale can be numeric and/or non-numeric. In some instances, a numeric score is initially calculated and then equated to a non-numeric score (e.g., "Satisfactory", "Good", "Needs Improvement", "Concerning", etc.). The criteria can include a range, an upper threshold, a lower threshold, a set of ranges or thresholds, or a function. For example, one criterion can specify that a "Satisfactory" rating will be assigned either if a population statistic is above a threshold or if the population statistic has improved by at least 20% relative to a comparable population statistic pertaining to less recent care.

In some instances, satisfaction engine 240 evaluates a set of check-point indicators in view of one or more satisfaction criteria. For example, satisfaction engine 240 can determine whether at least a threshold percentage of the indicators exceed (e.g., which, in various embodiments, can include exceeding in a positive or negative direction) a threshold.

In one instance, population quantifier 230 generates a score based on multiple check-point indicators, statistics, assessment of one or more check-point indicators and/or assessments of one or more statistics. For example, population quantifier 230 can generate a normalized statistic for each of a group of check-point indicators. A score can be a weighted sum of the normalized statistics. As another example, satisfaction engine 240 can produce a binary output, for each statistic related to each of a group of check-point indicators, indicating whether the statistic passes a satisfaction criterion. A score can be a weighted sum of the binary outputs.

After assessing satisfaction criteria, satisfaction engine 240 can identify one or more controllable parameters pertaining to a check-point indicator underlying the assessment. Satisfaction engine 240 can identify suggested changes to the controllable parameter(s) based on a satisfaction result. For example, a below-threshold result or unsatisfactory result can result in satisfaction engine 240 recommending a change to a controllable parameter in a first direction and an above-threshold result or satisfactory result can result in satisfaction engine 240 not recommending any change. In another example, a recommendation analysis extends beyond a binary assessment. For example, a satisfaction score in a first range can result in a recommendation to change a parameter in a first direction (e.g., to improve care), a score in a second range can result in no change recommendation, and a score in a third range can result in a recommendation to change a parameter in a second direction (e.g., to save costs).

A presentation engine 245 can present a population statistic, satisfaction criterion feature (e.g., threshold), satisfaction result, pertinent controllable parameter and/or suggested change to the pertinent controllable parameter to a reviewer 115. Presentation engine 245 can require authentication and/or a login before any such presentation. The presentation can include transmission of data to another device (e.g., a reviewer device 120), such that pertinent information can be presented at the other device.

In some instances, presentation engine 245 generates a report, the report including the statistic, satisfaction criterion feature, result, parameter and/or suggested change. The report can be stored in a reports data store 250 and presented to reviewer 115 (e.g., by presenting it on a page of an app or webpage, by presenting reviewer 115 with a link to download the report, or by emailing it to reviewer 115). The report can be presented routinely, upon a satisfaction analysis or upon determining that a satisfaction criterion was not met. In some instances, the report is dynamically (e.g., routinely being updated to show recent data) and can be presented substantially continuously.

The report can include graphs, tables, graphics and/or texts. In some instances, a population statistic is associated with a time period, such as a period during which a procedure was performed or a patient was released. A graph can then show how the statistic changes as the time period changes, to suggest, e.g., whether an institution is improving in its care. In some instances, a population statistic associated with a recent time period is presented, along with a satisfaction criterion feature (e.g., a target value) and a comparison statistic (e.g., to show any improvement within an institution and/or to show how an institution compares to other institutions). A report can further indicate how a population statistic was calculated or what it means. For example, it can describe a check-point indicator, indicate which types of cases were aggregated to calculate the statistic, identify a number of cases aggregated, include labels, etc. In one instance, the report identifies a current value for a check-point indicator, a target value for the check-point indicator, an indication as to whether the current value meets the target value and a suggested change to a controllable parameter if the target value is not met.

Thus, population quantifier 230 and satisfaction engine 240 provide the ability to monitor overall care (which can pertain to a specific time period, care line, institution, and/or patient group). Care management system 200 can also include a case-specific monitor 255 that monitors care on a case-specific basis. Specifically, case-specific monitor 255 can detect when a new value for a check-point indicator appears within a case. The value can then be assessed (e.g., immediately or within a short time window) in view of a satisfaction criterion. Case-specific monitor 255 can then (e.g., always or upon an unsatisfactory comparison) identify a pertinent controllable parameter and recommended changes to the parameter. Presentation engine 245 can generate a report identifying the case, the indicator and any recommended change to the controllable parameter. This report can be stored in report data store 250 and/or presented to a reviewer.

In some instances, case-specific details can also be presented to explain a population statistic or to detail a population. For example, a population statistic can indicate that 35% of cases having discharge dates within a time period at an institution had an unsatisfactory satisfaction result pertaining to a particular check-point indicator. A summary of each of all of the cases or some of the cases (e.g., those with unsatisfactory results or a random sampling) can simultaneously or subsequently (following a request for the summaries from a reviewer 115) can be presented. The summary can include value for variables, such as controllable parameters, check-point indicators and/or outcome results. The summary can further include characteristics of the patient and/or care (e.g., a date of the care, admission and/or discharge). In some instances, a summary of each case meeting a reviewer's query is presented (with or without a population statistic).

In one instance, a report is interactive, such that a reviewer can iteratively view information pertaining to various levels. For example, a report can initially show population statistics pertaining to a care line in a hospital. Upon receiving a corresponding reviewer request, population statistics can then be separately provided for one or each of a set of medical provider teams operating within the hospital. Upon receiving a corresponding reviewer request, population statistics can then be separately provided for one or each of a set of individual medical providers within a team. Check-point indicators supporting statistics can be presented alongside any presentation or, for example, upon receiving a corresponding request for such.

In one instances, population quantifier 230 performs a cross-level analysis to estimate which entity (and at which level) is likely responsible for one or more unsatisfactory or concerning population statistics or check-point indicators. For example, multiple doctors, nurses and departments may be associated with unsatisfactory population statistics. Population quantifier 230 can estimate that a medical-team-level problem is likely at the center of such statistics rather than any particular individual. The estimation can be performed by, for example, identifying a level with high cross-entity variability, identifying a level with a high cross-level value (e.g., population statistic), comparing variability amongst a set of entities at a lower level each of which corresponds to a single entity at a higher level, etc.

In some instances, presentation engine 245 can then present an identification of an entity (e.g., and a level of the entity) estimated to be responsible for unsatisfactory performance. The presentation can further include identifying population statistics and/or check-point indicators associated with the entity (e.g., and other entities at the level for comparison purposes) and/or associated with other related entities. For example, entities can be arranged in a hierarchy along various levels. Each entity can be connected to one or more other entities in other levels. Determining of population statistics for a higher level entity can involve aggregating check-point indicators associated with each of multiple lower level entities that are connected to the higher level entity. Thus, unsatisfactory indicators associated with one entity may result in degraded population statistics associated, not only with the entity, but also for other connected entities. Presentation engine 245 can identify information pertaining to the connected entities, such that a reviewer can see how a problem at one level corresponds to problems at other levels.

In some instances, presentation engine 245 can present reports and/or data to reflect substantially current data. For example, new case data can be represented in, presented and/or reported within a week, day, twelve hours, six hours, two hours, hour, fifteen minutes, minute, twenty second, five seconds or one second. In one instance, reports and/or data are updated in a real-time manner, such that presented reports and/or data relate to current operations of an entity. It will be appreciated that what constitutes real time can vary depending on a care line. For example, to characterize real-time operations of an operating room, data may need to be current within a five-minute window. Meanwhile, for a behavioral-health care line, less frequent updates (e.g., once a day) may sufficiently capture a current performance.

To timely update reports and/or data, various update-preparation actions can be performed. For example, at times corresponding to appropriate update times, case engine 205 can request case data from user devices, aggregator 225 can re-aggregate data (e.g., to include new data and/or to not include sufficiently old data), population quantifier 230 can generate one or more new population statistics or care score, satisfaction engine 240 can assess a new population statistic or care score, case-specific monitor 255 can analyze new case-specific data, population quantifier 230 and/or satisfaction engine 240 can identify any entities performing unsatisfactorily, and/or presentation engine 245 can update a report or generate a new report.

Figure 3:
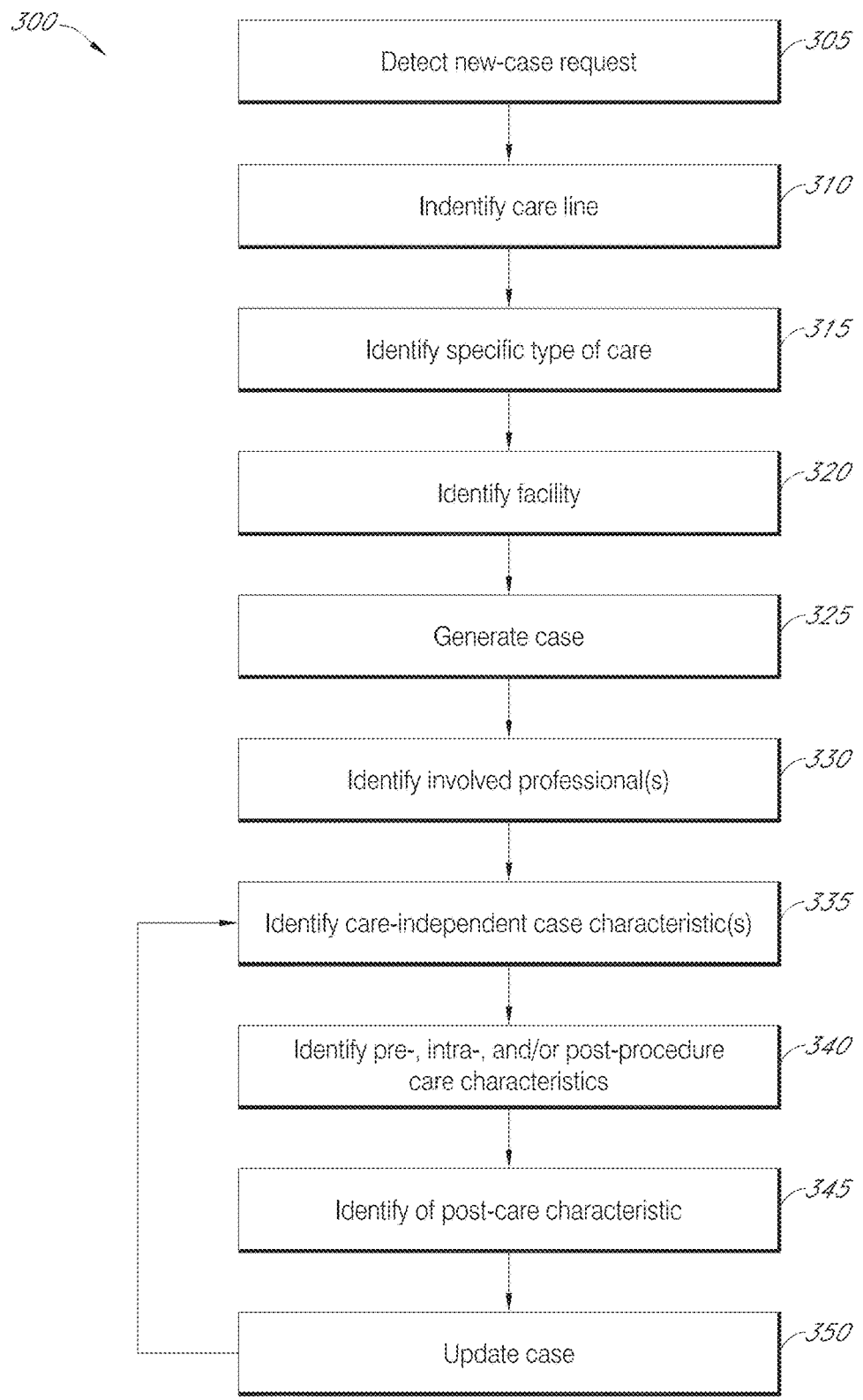
FIG. 3 illustrates a flowchart of an embodiment of a process for generating a medical-care case.

FIG. 3 illustrates a flowchart of an embodiment of a process 300 for generating a medical-care case. Process 300 begins at block 305, where case engine 205 detects a request from a user (e.g., via a website or app) for a new case to be generated. The request can include an express request (e.g., a selection of a 'new-case' button) or an implicit request (e.g., via a user uploading a file or beginning to enter information about a new patient or procedure).

Case engine 205 identifies a car line at block 310, a specific type of care (e.g., a specific procedure) at block 315 and a facility (e.g., one in which a patient is or will be admitted or one where care is being or will be provided) at block 320. The identifications can be based on, for example, user input (e.g., entering information or selecting from amongst a set of options), detecting corresponding information in an uploaded or received document (e.g., transmitted from a user device), and/or detecting information about a user device providing information and/or uploading documents (e.g., to identify an IP address to be associated with a particular facility).

Case engine 205 generates a case at block 325. Certain data may be required before a case will be generated, such as the data collected at one, more or all of blocks 310-320 and/or other data (e.g., date(s) of care, pre-care symptoms, patient-identifying information, etc.).

Case engine 205 identifies (e.g., via analysis of an uploaded or received document or user input) one or more professionals involved in the case's care (e.g., performing a procedure or providing pre- and/or post-procedure care) at block 330. The professionals can include physicians, surgeons, assistances, nurses, supervisors, and/or managers. Block 330 can further include an identification of how and/or when the identified professional(s) were, are or will be involved in the care.

Case engine 205 identifies (e.g., via analysis of an uploaded or received document or user input) a care-independent case characteristic (e.g., a patient's ailments, past procedures, current medications, weight, etc.) at block 335. Case engine 205 identifies (e.g., via analysis of uploaded documents, user input or data received from a medical device 130) a pre-, intra- and/or post-procedure care characteristic at block 340. Case engine 205 identifies (e.g., via analysis of an uploaded or received document or user input) a care-result characteristic at block 345.

One, more or all of the characteristics received at blocks 335-345 can be defined based on variables in variable data store 215. The characteristics can be received at substantially the same time (e.g., if a user is inputting data from a medical record or if they are included in a single document) or at various time points (e.g., as care progresses). The characteristics can be received from one or more user devices 110 and/or medical devices 130. Case engine 205 updates the case to include the received characteristic(s) at block 350. The update can occur as characteristics are received or at discrete time points (e.g., at regular intervals or prior to generating a report for a reviewer).

Figure 4:
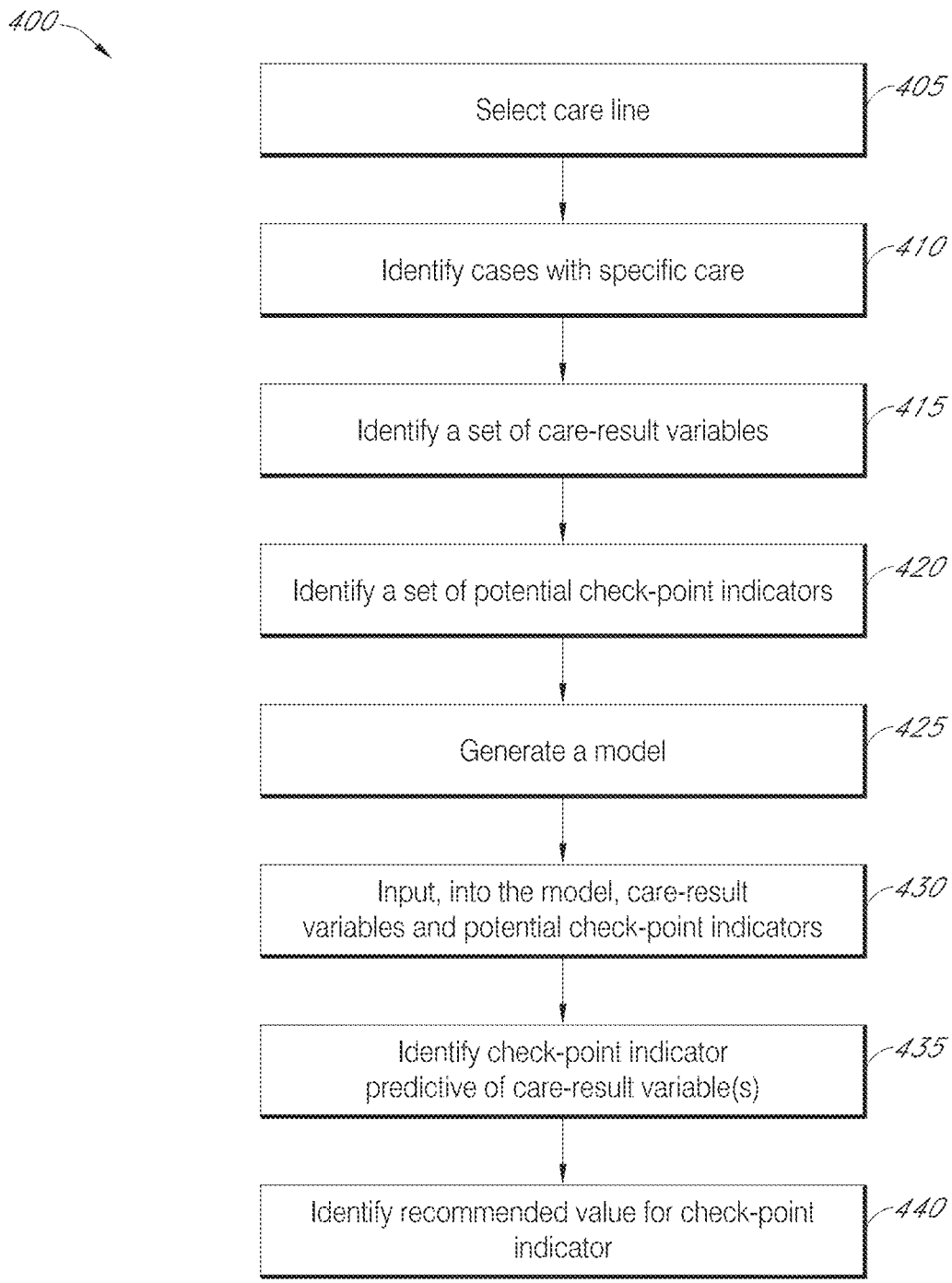
FIG. 4 illustrates a flowchart of an embodiment of a process for identifying check-point indicators to monitor.

FIG. 4 illustrates a flowchart of an embodiment of a process 400 for identifying check-point indicators to monitor. Process 400 begins at block 405, where care-line selector 220 selects a care line. Aggregator 225 identifies cases with specific care at block 410. Additional restrictions (e.g., identifying an institution, time period, type of procedure and/or patient characteristic) can also constrain which cases are identified at block 410. The identified cases can include those which are associated with dates sufficiently long ago to allow most subsequent care results caused by the care to have occurred. Population quantifier 230 identifies a set of care-result variables at block 415. The care result variables can be ones defined in variable data store 215 and/or identified by a user or reviewer. Population quantifier 230 identifies a set of potential check-point indicators at block 420. The potential check-point indicators can include some or all pre-, intra- and/or post-care characteristics. In some instances, the potential check-point indicators are characteristics defined by a user or reviewer as being a potential check-point indicator.

Population quantifier 230 generates a model at block 425. The model can be designed to identify which of a set of first variables are predictive (and a strength of any such prediction) of one or more second variables. The model can include, e.g., a learning algorithm, neural-net technique, and/or regression analysis. Population quantifier 230 inputs, into the model, the care result variables and the potential check-point indicators at block 430. In some instances, multiple care result variables are collapsed into a single metric, which is input into the model. The model can then produce output indicating which of the potential check-point indicators were correlated with or predictive of the care result variables and can, in some instances, further identify a significance and/or strength (or weight) of the correlation.

Variable selector 235 identifies a check-point indicator predictive of care result variable(s) at block 435. The indicator can be identified based on a weight or significance produced by the model. Variable selector 235 identifies a recommended value for the check-point indicator at block 440. The recommended value can include a threshold, a range bound, or a target. It can pertain to a population statistic. For example, if a check-point indicator is a surgery duration, the recommended value can include a case-specific duration threshold (e.g., "20 min") or a population statistic type and a range (e.g., "average weekly duration of 1-2 hours+/−30 minutes"). The value can be determined based on a sign of a relationship (e.g., correlation) between the indicator and one or more care-results. In some instances, recommended care result variable values are identified and a value of an indicator is back-calculated given model parameters. In some instances, simulations are run using a random or systematic array of possible indicator values to identify the value. Any of these processes can further consider practical constraints on the value and/or costs of extreme values (e.g., financial costs or time costs). Variables data store 215 can be updated to reflect the identified check-point indicator(s) and value(s).

It will be appreciated that part or all of process 400 can be periodically or routinely repeated. Thus, check-point indicators can be dynamic in their identity and can include those characteristics most predictive of quality-of-care results during recent time periods. It will be appreciated that, while process 400 includes one technique for identifying check-point indicators and recommended values in an at least partly automated manner, check-point indicators and recommended values can be defined using any of a variety of techniques and/or information. For example, a user can identify one or more check-point indicators for each of one or more care lines, and recommended values can be identified based on population statistics (e.g., to identify typical values or values associated with positive care-result variables) and/or based on user input.

Figure 5:
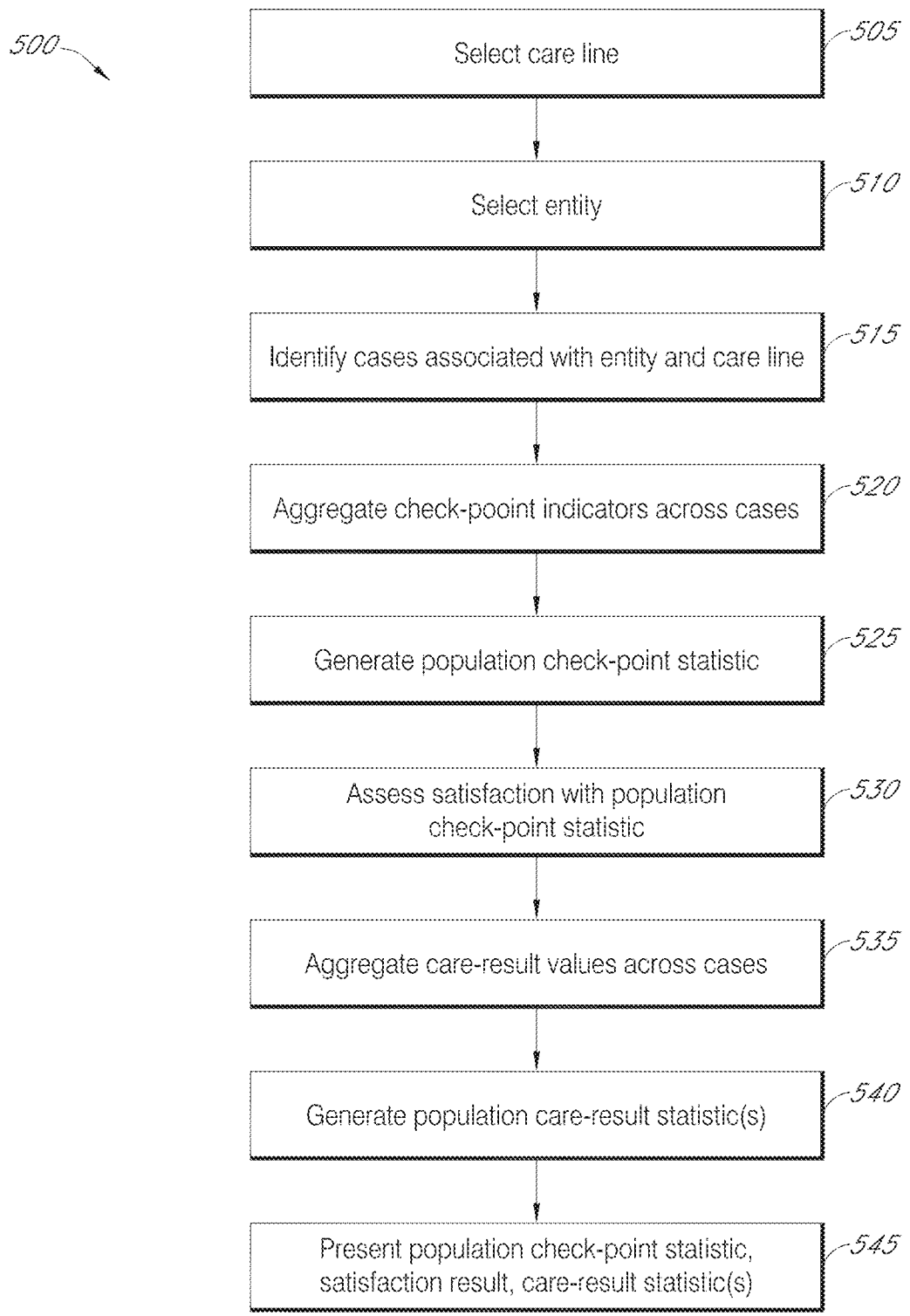
FIG. 5 illustrates a flowchart of an embodiment of a process for assessing medical care at a population level using check-point indicators.

FIG. 5 illustrates a flowchart of an embodiment of a process 500 for assessing medical care for a set of cases (e.g., applying to a particular entity) using check-point indicators. Process 500 begins at block 505, where care-line selector 220 selects a care line. Care-line selector 200 further selects an entity at block 510. The entity can include, for example, a facility (e.g., medical institution or hospital), a medical provider (e.g., a physician, technician or nurse), or a combination thereof. In some instances, block 510 includes selecting a group of entities (of same or different types), such as entities associated with a same or similar geographical region, supervising agency, insurance plan, owner, position, etc. The selections at blocks 505-510 can be based on, for example, input from a user or reviewer, automatically determined based on which reviewer is accessing a system, or determined based on data associated with a request (e.g., for a report) from a reviewer (e.g., identifying an entity associated with the reviewer or an entity identified in the request).

Aggregator 225 identifies cases associated with the care line and entity at block 515. Once again, the aggregation can be responsive to additional search constraints, such as time periods. For example, aggregator 225 can identify cases associated with an intensive-care unit at a specific hospital but can require that each case correspond to an instance where a patient was in the intensive-care ward within a previous week. As another example, aggregator 225 can identify cases, each corresponding to an instance where a patient was admitted to an emergency room on a current day and assigned to a particular physician.

Aggregator 225 aggregates check-point indicators across the identified cases at block 520. For example, aggregator 225 can generate a vector or matrix including the indicators. In some instances, aggregating the indicators can include aggregating each of multiple different check-point indicators (e.g., to produce a set of intake-time values and a set of times until physician evaluation values). In some instances, a check-point indicator may be unavailable for one or more cases. In one instance, such unavailability can be noted in an aggregated data structure. In one instance, the case can then be omitted from a present analysis pertaining to the care line and entity (e.g., though it may later be included upon availability of such indicator) or selectively from a present analysis pertaining only to the unavailable check-point indicator(s) (e.g., though it may contribute to one or more statistics corresponding to other check-point indicators).

Population quantifier 230 generates one or more population check-point statistics at block 525. Each population check-point statistic can correspond to a check-point indicator. When multiple population check-point statistics are generated, they may, or may not, include statistics of different types. For example, generated statistics can include an average and a maximum or a percentage (e.g., with above-threshold values) and a standard deviation.

Satisfaction engine 240 accesses variables data store 215 to identify a satisfaction criterion pertaining to the population check-point statistic. At block 530, satisfaction engine 240 assesses whether the criterion is met based on one or more population check-point statistics. In one instance, determining whether the satisfaction criterion is met corresponds to determining whether the population statistic matches a recommended value or range of values. The assessment can produce a satisfaction result, which can include, e.g., a numeric or textual result. In some instances, assessing satisfaction includes comparing one or more statistics to one or more thresholds (e.g., to determine whether a statistic exceeds a threshold or an extent to which a statistic does (or does not) exceed a threshold), comparing a statistic to one or more corresponding statistics (e.g., associated with other care lines), and/or comparing a statistic to a corresponding past statistic (e.g., to identify a change or acceleration in the statistic).

Aggregator 225 aggregates each of one or more care-result values (e.g., a value reflecting a prevalence (e.g., count or percentage) and/or severity of a complication, prevalence of readmission, prevalence and/or severity of readmission, etc.) across the identified cases at block 535. For example, aggregator 225 can generate a vector or matrix including the values. In some instances, a care-result value may be unavailable for one or more cases. In one instance, such unavailability can be noted in an aggregated data structure. In one instance, the case can then be omitted from a present analysis pertaining to the care line and entity (e.g., though it may later be included upon availability of such indicator) or selectively from a present analysis pertaining only to the unavailable care-result value(s) (e.g., though it may contribute to one or more statistics corresponding to other care-result values. In some instances, the cases used for the block 535 aggregation differ from those used for the block 520 aggregation (e.g., where cases for the block 535 aggregation may be associated with an over-lapping or non-overlapping later care time period). In some instances, the cases used for the block 535 aggregation differ from those used for the block 520 aggregation.

Population quantifier 230 generates one or more care-result statistics at block 540. Each generated population care-result statistic can correspond to a care result. When multiple population care-result statistics are generated, they may, or may not, include statistics of different types. For example, generated statistics can include an average and a maximum of a variable cost of care result for a care line and a percentage (e.g., with above-threshold values) and a standard deviation (e.g., for a same or different care result) for a length of stay care result for the care line.

In one instance, a care-result statistic includes a care score, which can be generated based on one or more of the generated population check-point statistics and/or based on one or more satisfaction assessments. In one instance, the care score is generated based on (or can include) a change in a population check-point statistic and/or satisfaction assessment. The care score can include, for example, a weighted (or unweighted) sum or average of a set of population check-point statistics or satisfaction results. Population quantifier 230 can further determine how the care score compares to care scores of other entities and/or time periods.

Presentation engine 245 presents one or more population check-point statistics, satisfaction results and/or care-result statistics at block 545. In some instances, presentation engine 245 generates a report to include the statistic(s), satisfaction result(s) and care-result statistic(s). In one instance, the report is configured to be interactive and may allow for the user to interact with the report to view various levels of detail (e.g., zeroing down on care provided by a particular institution, then a particular team, then a particular professional, then constraining a time period) or to understand different types of care. In one instance, the report is dynamic, such that presented values are periodically or continuously updated to reflect new cases and case updates.

In one instance, a report is structured to allow for a comparison between entities and/or care lines. For example, a population statistic for one entity can be represented amongst a distribution of corresponding statistics from other entities. As another example, a report can include care scores for a set of care lines for an entity. In one instance, a report is structured to allow for a temporal comparison. For example, a first background color of a care score can indicate that the care score is worse than one from a previous time period by a threshold amount, a second background color of a care score can indicate that the care score is better than one from a previous time period by a threshold amount, and a third (or no) background color can represent that the care score is the same as a previous care score (within a threshold amount). As another example, a line graph can show a time-series for each of one or more (e.g., normalized) population statistics for an entity over time (e.g., and can further identify recommended value thresholds for the statistics).

It will be appreciated that process 500 can (like all processes disclosed herein) be modified to include fewer, more or different blocks. For example, process 500 can further include assessing a satisfaction of one or more care results, population care-result statistics (e.g., pertaining to particular care results or an overall care score) and presenting a result of each of one or more of the assessments.

Figure 6:
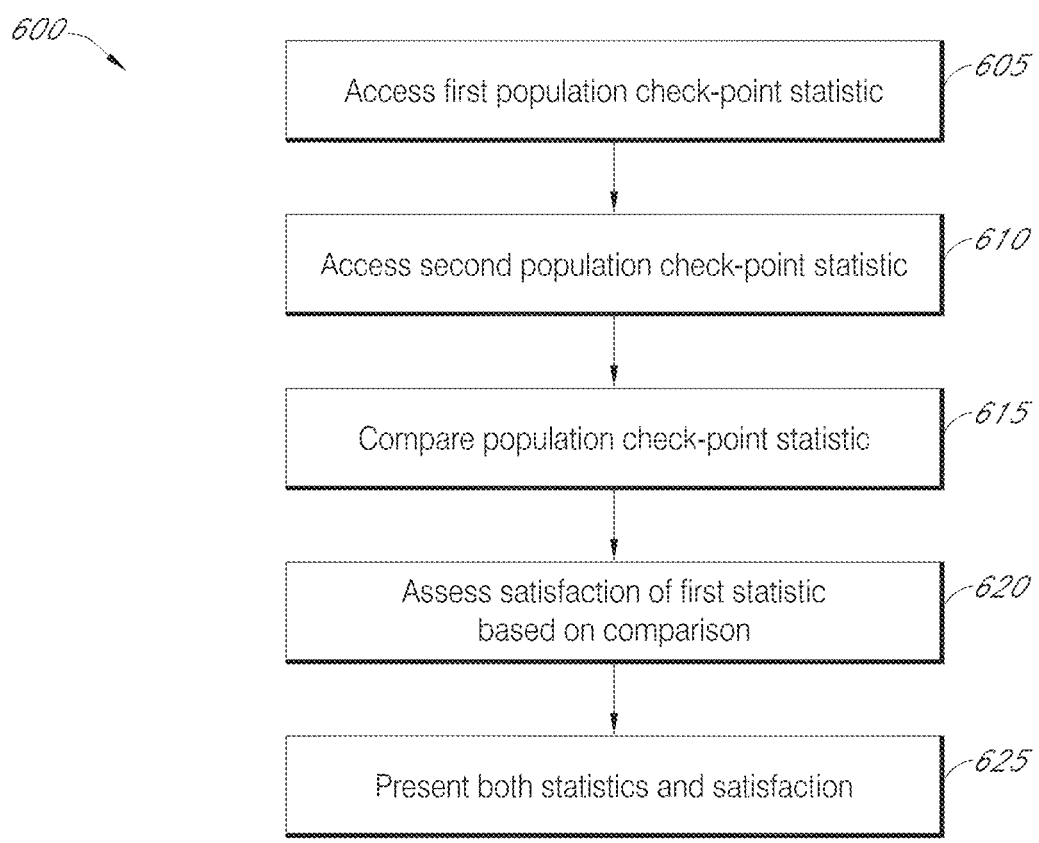
FIG. 6 illustrates a flowchart of an embodiment of a process for assessing medical care at a population level using check-point indicators.

FIG. 6 illustrates a flowchart of an embodiment of a process 600 for assessing medical care at a population level using check-point indicators. Process 600 begins at block 605, where satisfaction engine 240 accesses a first population check-point statistic at block 610. Satisfaction engine 240 accesses a second population check-point statistic at block 615. The first population check-point statistic can be one determined by population quantifier based on a first population of cases. The second population check-point statistic can be one determined by population quantifier based on a second population of cases. The two populations can be comparable but can vary in one respect, such as a time period (during which an institution admission occurred or procedure was performed), an institution, an involved professional, a patient characteristic (e.g., an age or weight) or a type of care provided within a care-line (e.g., an anesthesia used or a surgery-preparation measure). In some instances, the second population is larger than the first population. For example, the first population can be restricted to a single institution/professionals while the second can include all institutions/professionals. The statistics can be of a same type or similar types. In one instance, a statistic for the first population includes a single value and a statistic for the second population includes a range or variance (e.g., and potentially also a mean).

Satisfaction engine 240 compares the population checkpoint statistics to each other at block 620. The comparison can include a mathematical comparison, such as identifying which statistic is larger, an extent to which one statistic is larger than another, or whether the first statistic falls within a variance or range identified in the second statistic. Thus, this comparison can indicated how cases in the first population (e.g., relating to care provided by a particular institution or provided during a particular time period) fared relative to those in the second population (e.g., relating to a larger case dataset). Satisfaction engine 240 assesses satisfaction of first statistic based on the comparison at block 625. For example, it can be determined whether the first statistic is within a range or variance of the second statistic. Satisfaction engine 240 presents both statistics and a satisfaction result at block 630. The presentation can include presenting numbers, graphs and/or graphics.

It will be appreciated that process 600 can be modified to, for example, relate to care-result statistics and/or care scores instead of or in addition to check-point statistics.

Figure 7:
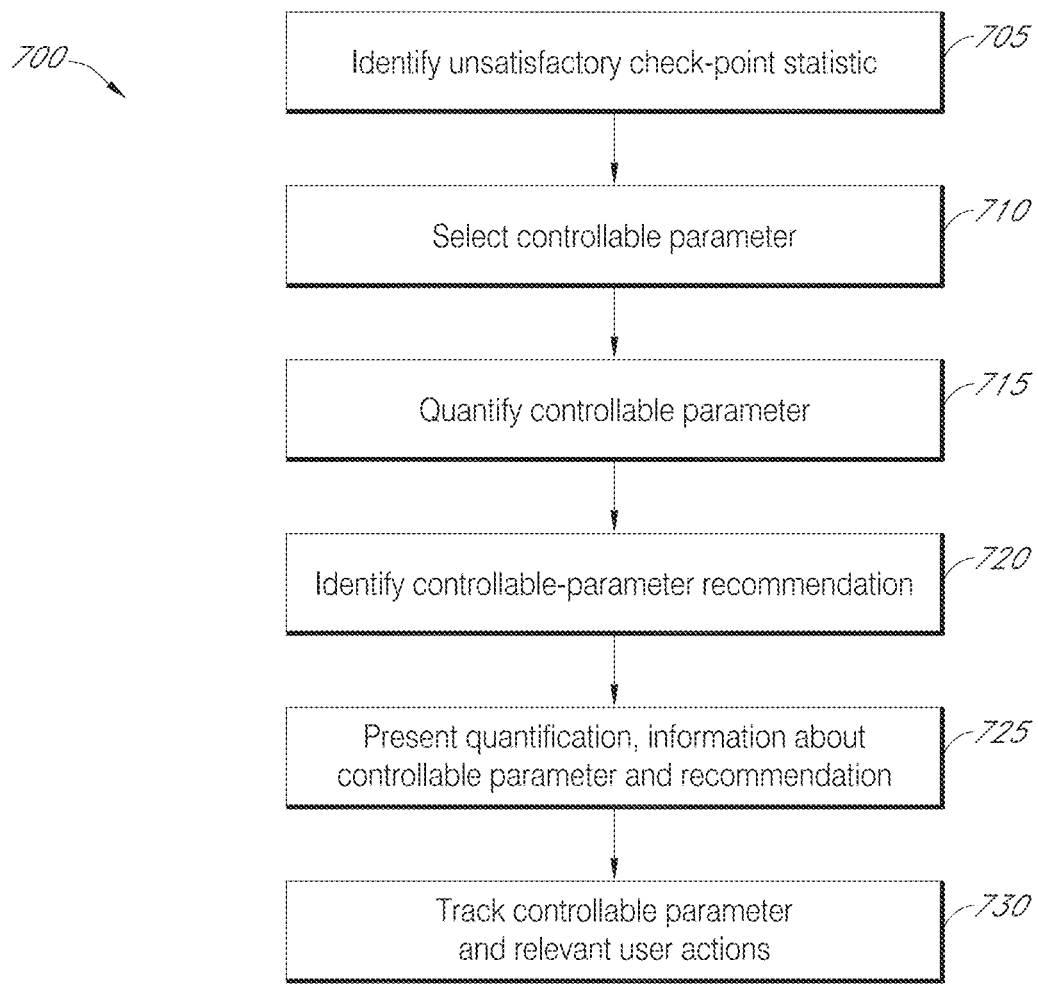
FIG. 7 illustrates a flowchart of an embodiment of a process for identifying controllable parameters pertaining to a check-point statistic of interest.

FIG. 7 illustrates a flowchart of an embodiment of a process 700 for identifying controllable parameters pertaining to a check-point statistic of interest. Process 700 begins at block 705, where satisfaction engine 240 identifies an unsatisfactory check-point statistic. The check-point statistic can include, for example, a value of a check-point indicator for a particular case or a value of a population statistic based on one or more check-point statistics. The statistic can correspond to one for which a corresponding satisfaction criterion was not satisfied and/or exceeded a threshold value. In some instances, the check-point statistic is determined to be unsatisfactory based on an analysis of the statistic absolutely. In some instances, the designation of the statistic being unsatisfactory results from an analysis comparing the statistic to one or more other statistics (e.g., one for a different time period and/or entity).

Satisfaction engine 240 selects a controllable parameter pertaining to the check-point statistic at block 710. This selection can be based on associations between check-point indicators and controllable parameters stored in variables data store 215. The associations can include automatically detected associations (e.g., identifying a correlation or other relationship between a number of nurses involved in an operation and a time of the operation) and/or associations identified by a user or reviewer. A controllable parameter can directly or indirectly influence a check-point indicator. For example, a controllable parameter can be proper administration of a blood-thinning medication, which could directly influence a check-point indicator indicating whether a blood-thinning medication was administered.

In some instances, population quantifier 230 quantifies the selected controllable parameter at block 715. The quantification can be performed using a same set of cases as those giving rise to the unsatisfactory check-point statistic or based on similar but more recent cases. For example, the quantification can include identifying a statistic for the controllable parameter that corresponds to the check-point statistic.

Satisfaction engine 240 identifies a recommendation pertaining to the controllable parameter at block 720. The recommendation can be based on the unsatisfactory statistic, the quantified parameter and/or the association. In some instances, the recommendation is based on a model relating controllable parameters to check-point indicators. Such a model can have properties similar to the model described in relation to FIG. 4. In some instances, a single model relates controllable parameters, check-point indicators and care results.

In one instance, identifying a recommendation includes selecting from amongst a set of recommendations. The selection can be based on which check-point statistic was identified at block 705, which controllable parameter was selected at block 710 and/or the quantification at block 715.

In one instance, a recommendation can relate to data availability, which can include (for example) changing monitoring (e.g., to increase frequency or change times of monitoring particular health data), changing data presentation (e.g., to ensure that particular reviewers quickly receive data) and/or changing a statistic calculation technique (e.g., to use smaller time windows to calculate statistics and/or to increase a weight for recent data). In one instance, a recommendation can relate to a management structure, which can include (for example) changing who is in charge of making particular decisions, a quantity of work or decisions assigned to one or more particular individuals or types of individuals or an authority given to one or more individuals (e.g., to be able to contribute to or individually make particular types of health decisions).

In one instance, a recommendation can relate changing an aspect of care development, such as a protocol for providing care to a given patient group (e.g., a type of post-operative care provided or a length of an in-hospital monitoring period). In one instance, a recommendation can relate to changing an aspect of care delivery (e.g., changing who is assigned to provide particular types of care, changing a number of people assigned to assist in a type of care or changing whether a type of care is to be delivered as in- or out-patient care). In one instance, a recommendation can relate to changing an aspect of a supply chain (e.g., changing a protocol for requesting a medication from a pharmacy or routing a medication from a pharmacy to an administer of the medication). In one instance, a recommendation can relate to changing an aspect of education (e.g., providing education pertaining to post-operative limitations or medication limitations to a patient, providing information pertaining to appropriate medication-dosage determinations to nurses or providing information about patient-group definitions to a physician).

Presentation engine 245 presents the controllable-parameter quantification, information about the controllable parameter and/or the recommendation to a reviewer 115 at block 725. This presentation can be via a report, email, webpage, app page, text message, etc. Reviewer 115 can include on who initiated a reviewing process and/or one associated with the recommendation. In one instance, a communication is sent to a system automatically effect the recommendation (e.g., to change a frequency of monitoring a health variable or to change a number of health professionals assigned to an event). In one instance, presenting a recommendation includes presenting a one- or multi-step action plan.

Satisfaction engine 240 tracks values for the controllable parameter, whether the recommendation was seemingly or known to have been effected (and, potentially, an extent or type of the recommendation implementation) and relevant user actions at block 730.

It will be appreciated that process 700 can be modified to, for example, identify an unsatisfactory care-result value instead off an unsatisfactory check-point statistic at block 705. The controllable parameter selected at block 710 can then be one associated with the care result.

Figure 8:
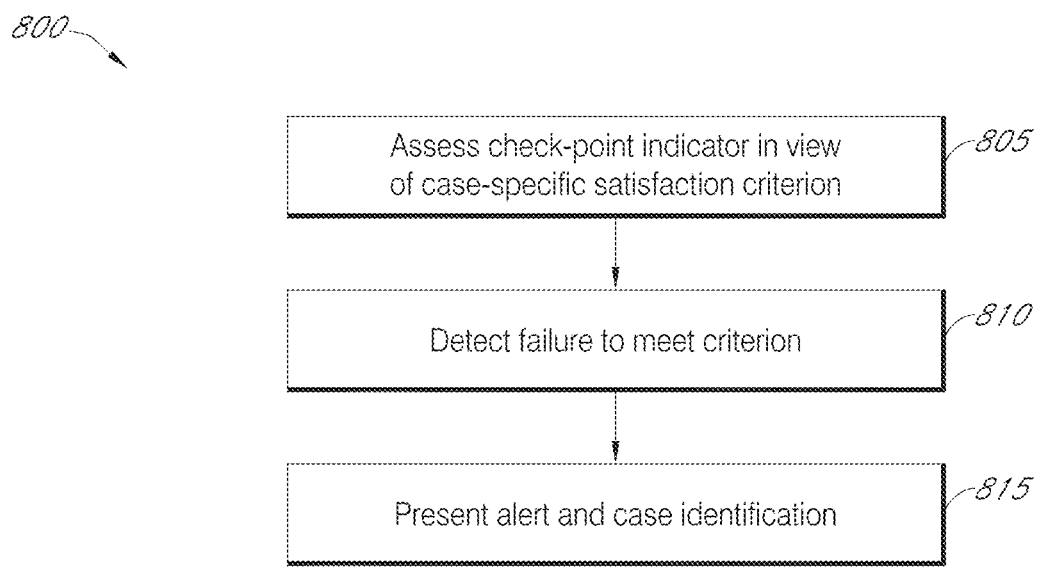
FIG. 8 illustrates a flowchart of an embodiment of a process for assessing medical care at a case-specific level.

FIG. 8 illustrates a flowchart of an embodiment of a process 800 for assessing medical care at a case-specific level. Process 800 begins at block 805, where case-specific monitor 255 assesses a check-point indicator for a case in view of a case-specific satisfaction criterion. The assessment can occur substantially continuously, at routine intervals or upon detecting a change (e.g., detecting entry of a value of a case characteristic by a user). It will be appreciated that a check-point indicator monitored and/or assessed for individual cases and/or a case-specific satisfaction criterion can be the same as or different from a check-point indicator and/or satisfaction criterion used for population analysis. The assessment can include, e.g., comparing the indicator to one or more thresholds, quantifying a change (e.g., temporal derivative) in the indicator, and/or calculating a satisfaction score. In one instance, the assessment can include comparing the indicator to one or more other indicators, such as a corresponding indicator associated with a different entity and/or time period.

Case-specific monitor 255 detects a failure to meet the criterion at block 810. For example, the detection can include detecting an unsatisfactory rating, determining that a satisfaction score is below a threshold, and/or detecting a negative change in a satisfaction rating.

Presentation engine 245 generates an alert and presents the alert (e.g., to a reviewer 115) at block 815. The alert can be presented by, e.g., presenting the alert on a webpage or app page, emailing the alert, paging a reviewer, texting the alert, etc. The alert can identify the case at issue (e.g., including a name of a patient), the check-point indicator assessed, an indication of the failure to meet the criterion, a proposed change in an indicator-related controllable feature, and/or an identification of the indicator-related controllable feature.

In some embodiments, a care management system is provided for identifying intra-care characteristics indicative of a caliber of medical care being provided to patients. A case data store includes a plurality of cases. Each case of the plurality of cases identifies a patient, a type of a medical care received by the patient, a set of potential check-point indicators, and a care result variable. Each potential check-point indicator of the set of potential check-point indicators characterizes a feature of the medical care received by the patient or a health characteristic of the patient during a provision of the medical care. (In some instances, one, more of each potential check-point indicator of the set of potential check-point indicators cannot practically be directly controlled by a provider of the medical care.) The care result variable identifies whether an event occurred after or during the provision of the medical care, the event relating to the patient's health and being indicative of a quality of the medical care. An aggregator identifies a set of cases from amongst the plurality of cases. Each case of the set of cases identifies a same type of medical care. A population quantifier accesses, from each case in the set of cases, the set of potential check-point indicators and the care result variable. The population quantifier further inputs the sets of potential check-point indicators and the care result variables from the set of cases into a model. The population quantifier further executes the model. Execution of the model produces an output indicating, for each of the potential check-point indicators from the set of potential check-point indicators, whether the potential check-point indicator is predictive of the care result variable. A variable selector identifies a potential check-point indicator of the set of potential check-point indicators as being a check-point indicator based on the determination of the model. In some instances, the variable selector further identifies a satisfaction criterion for the check-point indicator, and the satisfaction criterion includes a value.

In some embodiments, a care management system is provided for identifying intra-care characteristics indicative of a caliber of medical care being provided to patients. A case data store includes a plurality of cases. Each case of the plurality of cases identifies a patient, a type of a medical care received by the patient, an entity that provided the medical care, a set of potential check-point indicators, and a care result variable. Each potential check-point indicator of the set of potential check-point indicators characterizes a feature of the medical care received by the patient or a health characteristic of the patient during a provision of the medical care. (In some instances, one, more of each potential check-point indicator of the set of potential check-point indicators cannot practically be directly controlled by a provider of the medical care.) The care result variable identifies whether an event occurred after or during the provision of the medical care. The event relates to the patient's health and being indicative of a quality of the medical care. An aggregator identifies a first set of cases from amongst the plurality of cases. Each case of the first set of cases identifies a same type of medical care and a first entity. The aggregator also identifies a second set of cases from amongst the plurality of cases. Each case of the second set of cases identifies a same type of medical care and a second entity. A population quantifier, for each set of the first set of cases and the second set of cases: accesses, from each case in the set of cases (the set of potential check-point indicators and the care result variable), inputs the sets of potential check-point indicators and the care result variables from the set of cases into a model, and executes the model. Execution of the model produces an output indicating, for each of the potential check-point indicators from the set of potential check-point indicators, whether the potential check-point indicator is predictive of the care result variable. A variable selector identifies, for each set of the first set of cases and the second set of cases, a potential check-point indicator of the set of potential check-point indicators as being a check-point indicator based on the determination of the model. A first check-point indicator identified by the population quantifier using the first set of cases differs from a second check-point indicator identified by the population quantifier using the second set of cases. In some instances, the variable selector further determines a first satisfaction criterion for the first check-point indicator. The first satisfaction criterion includes a first value. The variable selector can also determine a second satisfaction criterion for the second check-point indicator, the second satisfaction criterion including a second value.

In some embodiments, a care management system is provided for identifying intra-care characteristics indicative of a caliber of medical care being provided to patients. A case data store includes a plurality of cases. Each case of the plurality of cases identifies a patient, a type of a medical care received by the patient, a set of potential check-point indicators, and a set of care result variables. Each potential check-point indicator of the set of potential check-point indicators characterizes a feature of the medical care received by the patient or a health characteristic of the patient during a provision of the medical care. (In some instances, one, more of each potential check-point indicator of the set of potential check-point indicators cannot practically be directly controlled by a provider of the medical care.) Each care result variable of the set of care result variables identifies whether an event occurred after or during the provision of the medical care, the event relating to the patient's health and being indicative of a quality of the medical care. An aggregator identifies a set of cases from amongst the plurality of cases. A population quantifier accesses, from each case in the set of cases, the set of potential check-point indicators and the set of care result variables and inputs the sets of potential check-point indicators and the sets of care result variables from the set of cases into a model. The population quantifier further executes the model. Execution of the model produces an output indicating, for each of the potential check-point indicators from the set of potential check-point indicators, whether the potential check-point indicator is predictive of a net care result. The net care result depends on each care result variable of the set of care result variables. A variable selector identifies a potential check-point indicator of the set of potential check-point indicators as being a check-point indicator based on the determination of the model. In some instances, the variable selector further identifies a satisfaction criterion for the check-point indicator, the satisfaction criterion including a value.

In some embodiments, a care management system is provided for monitoring a caliber of medical care being provided to patients. A case data store includes a plurality of cases. Each case of the plurality of cases identifies a patient, a type of a medical care received by the patient, a check-point indicator and an entity that provided the medical care. The check-point indicator characterizes a feature of the medical care received by the patient or a health characteristic of the patient during a provision of the medical care. (In some instances, the check-point indicator of the set of potential check-point indicators cannot practically be directly controlled by a provider of the medical care.) The check-point indicator is predictive of a care result variable. An aggregator identifies a first set of cases and a second set of cases from amongst the plurality of cases. For each case in the first set of cases, a first entity provided the medical care. For at least one case in the second set of cases, a second entity provided the medical care. The cases in both the first and second sets identify a same type of medical care. A population quantifier generates a first population check-point statistic based on the check-point indicators identified in the first set of cases and generates a second population check-point statistic based on the check-point indicators identified in the second set of cases. A presentation engine simultaneously presents the first population check-point statistic and the second population check-point statistic. In some instance, for at least a second case in the second set of cases, the first entity provided the medical care. In some instances, the first entity comprises a first medical institution and the second entity comprises a second medical institution.

In some embodiments, a care management system is provided for monitoring a caliber of medical care being provided to patients. A case data store includes a plurality of cases. Each case of the plurality of cases identifies a patient, a type of a medical care received by the patient, a check-point indicator and a time identifier. The check-point indicator characterizes a feature of the medical care received by the patient or a health characteristic of the patient during a provision of the medical care. (In some instances, the check-point indicator of the set of potential check-point indicators cannot practically be directly controlled by a provider of the medical care.) An aggregator identifies a set of cases from amongst the plurality of cases, the set of cases having similar time identifiers and a same type of medical care. A population quantifier generates a population check-point statistic based on the check-point indicators identified in the set of cases. A satisfaction engine accesses a satisfaction criterion pertaining to the check-point indicator, and determines that the satisfaction criterion is not met based on the population check-point statistic. A presentation engine presents an indication that the satisfaction criterion is not met.

In some embodiments, a care management system is provided for monitoring a caliber of medical care being provided to patients. A case data store includes a plurality of cases. Each case of the plurality of cases identifies a patient, a type of a medical care received by the patient, a check-point indicator and a time identifier. The check-point indicator characterizes a feature of the medical care received by the patient or a health characteristic of the patient during a provision of the medical care. (In some instances, the check-point indicator of the set of potential check-point indicators cannot practically be directly controlled by a provider of the medical care.) An aggregator identifies a set of cases from amongst the plurality of cases. The set of cases have similar time identifiers and a same type of medical care. A population quantifier generates a population check-point statistic based on the check-point indicators identified in the set of cases. A satisfaction engine accesses a first satisfaction criterion pertaining to the check-point indicator and determines a first satisfaction result that indicates whether the first satisfaction criterion is met based on the population check-point statistic. A satisfaction engine further accesses a second satisfaction criterion pertaining to the check-point indicator, the first satisfaction criterion being different from the second satisfaction criterion and determines a second satisfaction result that indicates whether the second satisfaction criterion is met based on a check-point indicator identified in a case. A presentation engine presents the first satisfaction result and the second satisfaction result. In some instances, the presentation engine presents the first satisfaction result and the second satisfaction result at different times.

In some embodiments, a care management system is provided for monitoring a caliber of medical care being provided to patients. A case data store includes a plurality of cases. Each case of the plurality of cases identifies a patient, a type of a medical care received by the patient and a check-point indicator. The check-point indicator characterizes a feature of the medical care received by the patient or a health characteristic of the patient during a provision of the medical care. An aggregator identifies a set of cases from amongst the plurality of cases. Each of the set of cases are associated with a similar time and a same type of medical care. A population quantifier generates a population check-point statistic based on the check-point indicators identified in the set of cases. A satisfaction engine accesses a satisfaction criterion pertaining to the check-point indicator and determines that the satisfaction criterion is not met based on the population check-point statistic. The satisfaction engine further identifies a controllable parameter that is known or estimated to have influence over the check-point indicator and identifies a suggested modification pertaining to the controllable parameter to improve the check-point indicator. A presentation engine presents the suggested modification to the controllable parameter. In some instances, the identification of the controllable parameter includes selecting the controllable parameter from amongst a set of controllable parameter, where each controllable parameter in the set of controllable parameter is known or estimated to have influence on the check-point indicator, and the selection being based on the population check-point statistic.

Figure 9:
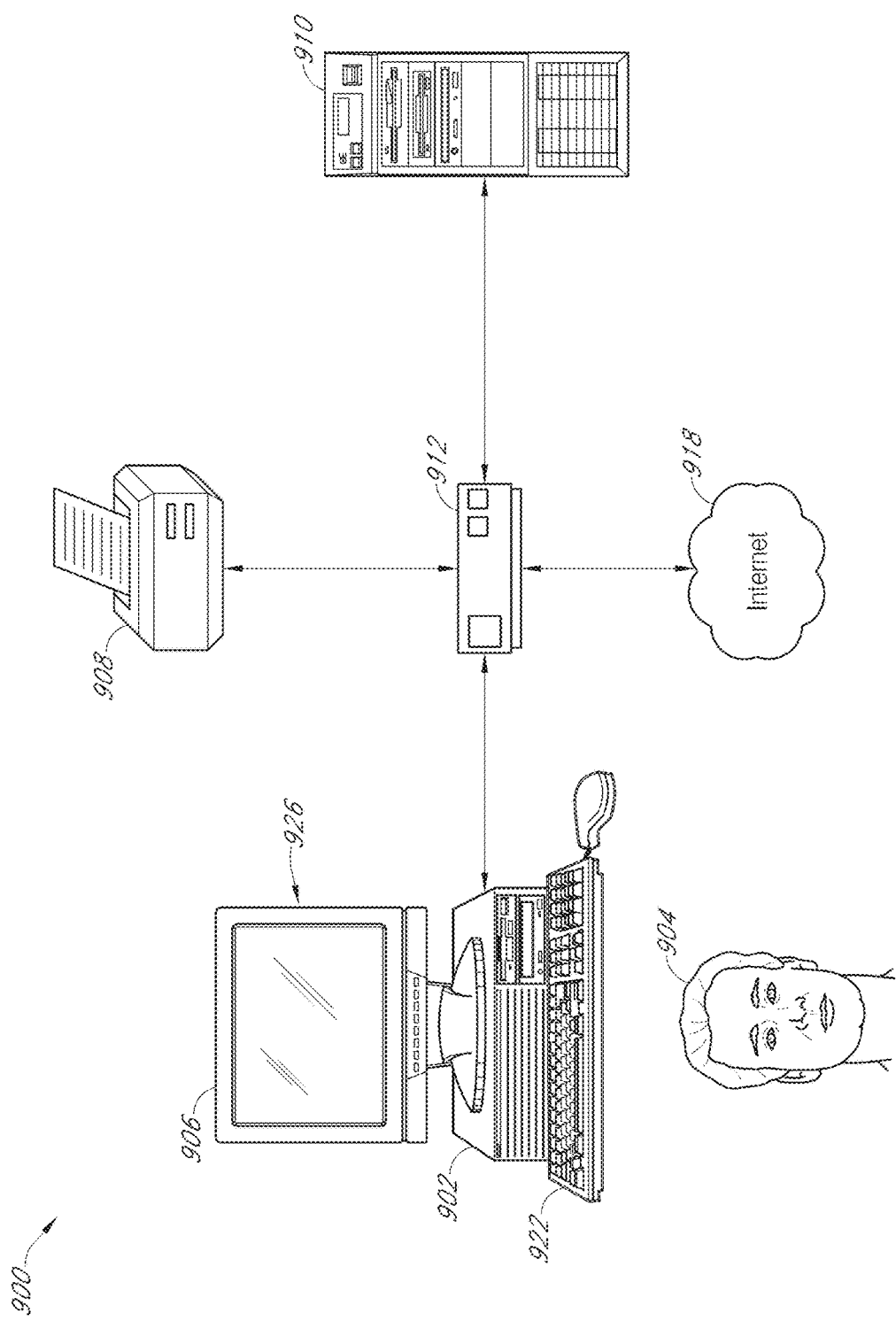
FIG. 9 depicts a block diagram of an embodiment of a computer system.

Referring next to FIG. 9, an exemplary environment with which embodiments can be implemented is shown with a computer system 900 that can be used by a designer 904 to design, for example, electronic designs. The computer system 900 can include a computer 902, keyboard 922, a network router 912, a printer 908, and a monitor 906. The monitor 906, processor 902 and keyboard 922 are part of a computer system 926, which can be a laptop computer, desktop computer, handheld computer, mainframe computer, etc. Monitor 906 can be a CRT, flat screen, etc.

A designer 904 can input commands into computer 902 using various input devices, such as a mouse, keyboard 922, track ball, touch screen, etc. If the computer system 900 comprises a mainframe, a designer 904 can access computer 902 using, for example, a terminal or terminal interface. Additionally, computer system 926 can be connected to a printer 908 and a server 910 using a network router 912, which can connect to the Internet 918 or a WAN.

Server 910 can, for example, be used to store additional software programs and data. In one embodiment, software implementing the systems and methods described herein can be stored on a storage medium in server 910. Thus, the software can be run from the storage medium in server 910. In another embodiment, software implementing the systems and methods described herein can be stored on a storage medium in computer 902. Thus, the software can be run from the storage medium in computer system 926. Therefore, in this embodiment, the software can be used whether or not computer 902 is connected to network router 912. Printer 908 can be connected directly to computer 902, in which case, computer system 926 can print whether or not it is connected to network router 912.

Figure 10:
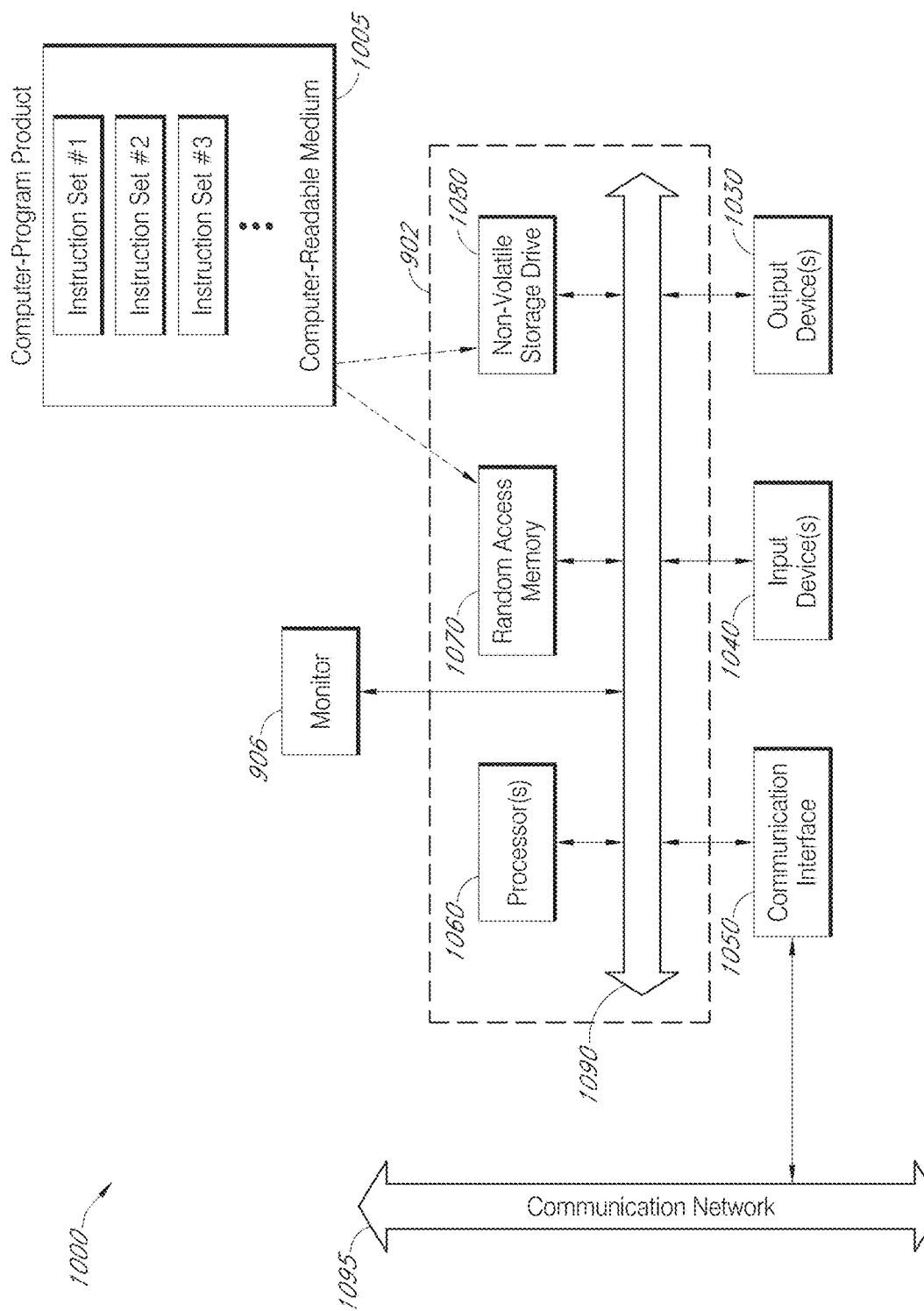
FIG. 10 depicts a block diagram of an embodiment of a special-purpose computer system.

With reference to FIG. 10, an embodiment of a special-purpose computer system 1000 is shown. Care management system 150 and/or any components thereof are examples of a special-purpose computer system 1000. Thus, for example, one or more special-purpose computer systems 1000 can be used to provide the function of care management system 150. The above methods can be implemented by computer-program products that direct a computer system to perform the actions of the above-described methods and components. Each such computer-program product can comprise sets of instructions (codes) embodied on a computer-readable medium that directs the processor of a computer system to perform corresponding actions. The instructions can be configured to run in sequential order, or in parallel (such as under different processing threads), or in a combination thereof. After loading the computer-program products on a general purpose computer system 926, it is transformed into the special-purpose computer system 1000.

Special-purpose computer system 1000 comprises a computer 902, a monitor 906 coupled to computer 902, one or more additional user output devices 1030 (optional) coupled to computer 902, one or more user input devices 1040 (e.g., keyboard, mouse, track ball, touch screen) coupled to computer 902, an optional communications interface 1050 coupled to computer 902, a computer-program product 1005 stored in a tangible computer-readable memory in computer 902. Computer-program product 1005 directs system 1000 to perform the above-described methods. Computer 902 can include one or more processors 1060 that communicate with a number of peripheral devices via a bus subsystem 1090. These peripheral devices can include user output device(s) 1030, user input device(s) 1040, communications interface 1050, and a storage subsystem, such as random access memory (RAM) 1070 and non-volatile storage drive 1080 (e.g., disk drive, optical drive, solid state drive), which are forms of tangible computer-readable memory.

Computer-program product 1005 can be stored in non-volatile storage drive 1090 or another computer-readable medium accessible to computer 902 and loaded into memory 1070. Each processor 1060 can comprise a microprocessor, such as a microprocessor from Intel® or Advanced Micro Devices, Inc®, or the like. To support computer-program product 1005, the computer 902 runs an operating system that handles the communications of product 1005 with the above-noted components, as well as the communications between the above-noted components in support of the computer-program product 1005. Exemplary operating systems include Windows® or the like from Microsoft Corporation, Solaris® from Sun Microsystems, LINUX, UNIX, and the like.

User input devices 1040 include all possible types of devices and mechanisms to input information to computer system 902. These can include a keyboard, a keypad, a mouse, a scanner, a digital drawing pad, a touch screen incorporated into the display, audio input devices such as voice recognition systems, microphones, and other types of input devices. In various embodiments, user input devices 1040 are typically embodied as a computer mouse, a trackball, a track pad, a joystick, wireless remote, a drawing tablet, a voice command system. User input devices 1040 typically allow a user to select objects, icons, text and the like that appear on the monitor 906 via a command such as a click of a button or the like. User output devices 1030 include all possible types of devices and mechanisms to output information from computer 902. These can include a display (e.g., monitor 906), printers, non-visual displays such as audio output devices, etc.

Communications interface 1050 provides an interface to other communication networks and devices and can serve as an interface to receive data from and transmit data to other systems, WANs and/or the Internet 918. Embodiments of communications interface 1050 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 1050 can be coupled to a computer network, to a FireWire® bus, or the like. In other embodiments, communications interface 1050 can be physically integrated on the motherboard of computer 902, and/or can be a software program, or the like.

RAM 1070 and non-volatile storage drive 1080 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 1070 and non-volatile storage drive 1080 can be configured to store the basic programming and data constructs that provide the functionality of various embodiments of the present invention, as described above.

Software instruction sets that provide the functionality of the present invention can be stored in RAM 1070 and non-volatile storage drive 1080. These instruction sets or code can be executed by processor(s) 1060. RAM 1070 and non-volatile storage drive 1080 can also provide a repository to store data and data structures used in accordance with the present invention. RAM 1070 and non-volatile storage drive 1080 can include a number of memories including a main random access memory (RAM) to store of instructions and data during program execution and a read-only memory (ROM) in which fixed instructions are stored. RAM 1070 and non-volatile storage drive 1080 can include a file storage subsystem providing persistent (non-volatile) storage of program and/or data files. RAM 1070 and non-volatile storage drive 1080 can also include removable storage systems, such as removable flash memory.

Bus subsystem 1090 provides a mechanism to allow the various components and subsystems of computer 902 communicate with each other as intended. Although bus subsystem 1090 is shown schematically as a single bus, alternative embodiments of the bus subsystem can utilize multiple busses or communication paths within computer 902.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure. Similarly, select examples are provided below, and it will be appreciated that the examples are illustration of select embodiments of the disclosures presented herein.

EXAMPLES

Examples below relate to potential exemplary care-related monitoring techniques. FIGS. 11-16 show interactive presentations, which include monitored care data, analysis of care data and options for reviewers to specify presentation characteristics and/or recommendations to implement.

Example 1

A set of care lines are defined to include: acute myocardial infarction response, hip replacement, knee replacement, spinal surgery, sepsis response, coronary artery bypass grafting (CABG), and stroke response. Further, a set of care results are identified to include an incidence of mortality, occurrence of complications, contraction of hospital-acquired conditions, readmission to an institution, cost of care, variance of cost of care, and/or length of admission. For each of the care lines, a set of check-point indicators are identified as well as a target for the indicator.

A dynamic presentation is generated. A first presentation component identifies each care line and shows a numeric care score for each care line. A reviewer selects the CABG care line by clicking on a representation of the care line. A graph shows a time-series for the CABG care line, where each point corresponds to a score for the care line corresponding to a particular month in the last year. Overlaid with the time-series curve is another curse for the previous year. The presentation component further includes an indication (e.g., an arrow and color) indicting that a current care score for the CABG care line is lower than a care score from a previous time point and for a corresponding time period within a previous year.

A second presentation component identifies each of the care results and shows a numeric value for each care result. A reviewer selects the hospital-acquired condition (HAC) result. In response, a time-series graph is shown. A first curve shows a median value at each month for the HAC result, a second curve shows a maximum value, a third curve shows a minimum and a fourth shows a median value from a previous year. The presentation further includes an indication (e.g., an arrow and color) indicting that a current care-result value for the HAC result is lower than a care score from a previous time point and is the same as that for a corresponding time period within a previous year.

A third presentation component identifies each of a set of check-point indicators (a value relating to each of when an antibiotic was discontinued, a regularity of antibiotic administration, appropriate selection of an antibiotic, whether and/or an extent to which atrial fibrillation occurred, whether a ventilator was used, a consistency and/or an extent to which blood glucose is managed, whether and which blood products were used, and whether a Foley catheter was timely and appropriately removed). Each of the indicators correspond to a selected care line and/or care result. A reviewer selects the ventilator indicator, and a graph and comparative indicators are shown (e.g., with similar line graphs and comparative indications).

Figure 11:
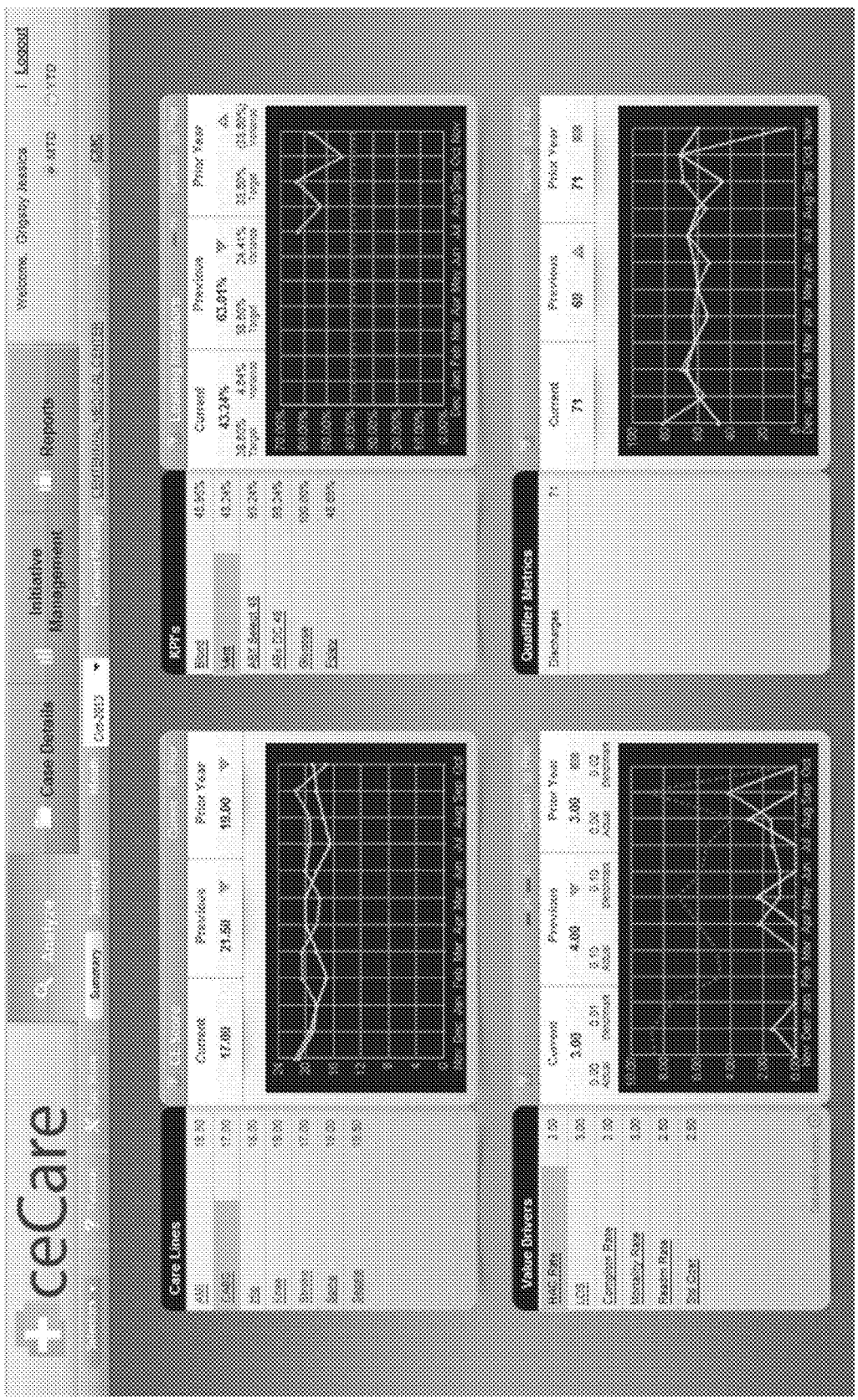

The presentation components can be presented simultaneously or sequentially. FIG. 11 shows an example of a presentation with the exemplary presentation components for an exemplary hospital.

Example 2

A reviewer changes a view to a comparative view. A first presentation component identifies each of a set of care lines. For each care line, a line graph is presented to show how a care score for the care line changed over time. Further, a current value for the care score is shown, along with a care score from a previous month, a care score from a previous year (in a corresponding month) and a current patient count associated with the line. A reviewer has an option of viewing similar data for each check-point indicator associated with a single care line.

A reviewer selects the CABG care line from the first component. A second presentation component includes a bar graph that compares the care score for the line for the relevant entity to a corresponding care score based on different cases. For example, the care score for a hospital can be compared to that from a group of hospitals, a division of hospitals and all hospitals with a particular owner.

A third presentation component identifies each of a set of care results for a selected line and a value for each result. A reviewer selects one result, and a line graph shows how the result has progressed throughout a past year. A reviewer has an option to instead view how a value for the care result compares to corresponding values from other entities.

A fourth presentation component includes a bar graph that shows values for the care result for each of a set of diagnosis-related groups. A superimposed line graph further identifies a patient count in each group. A reviewer has an option of selecting an option to change the break-down to, rather than being based on the diagnosis-related groups, be based on another variable, such as physician, procedure and/or service line.

Figure 12:
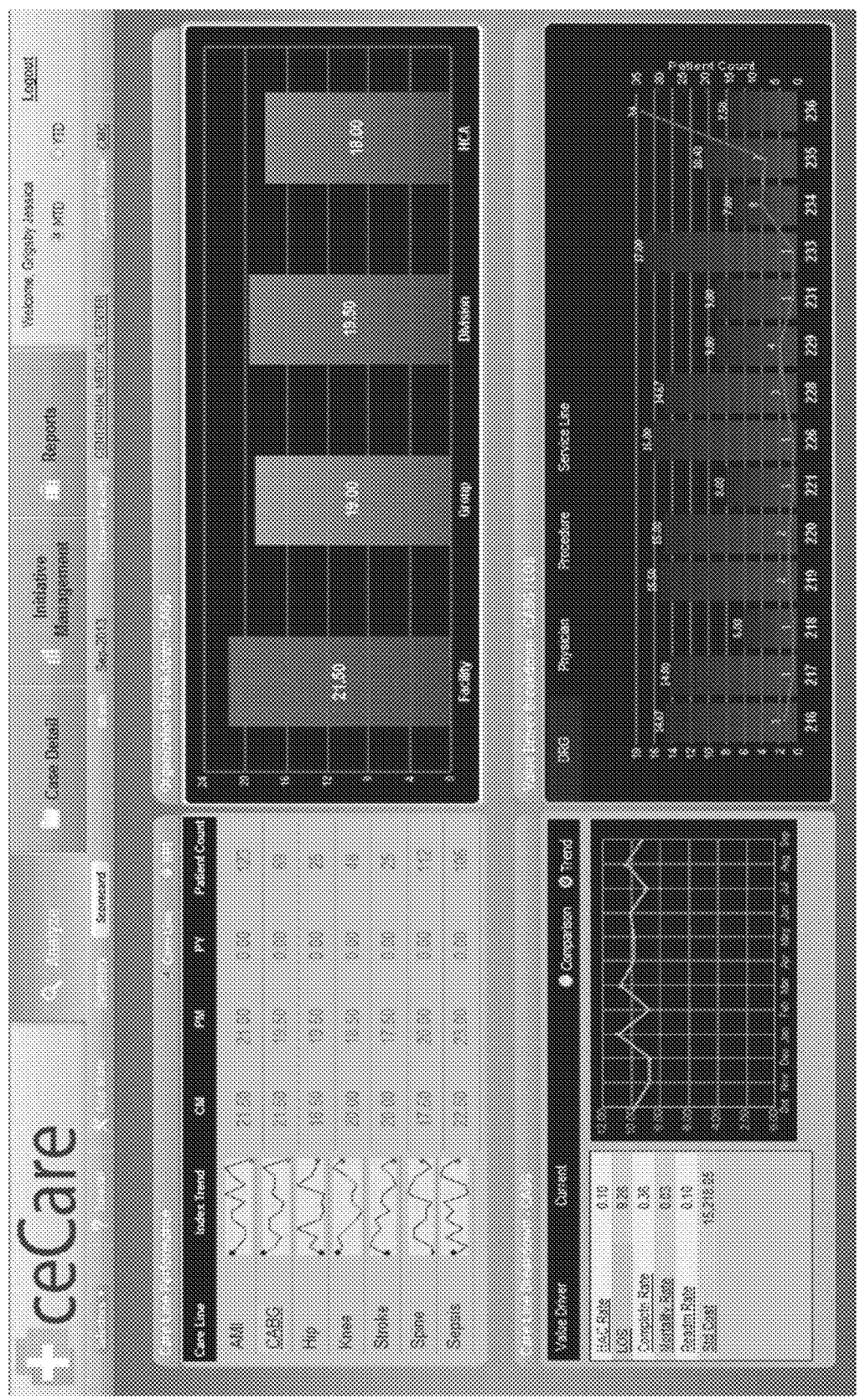

The presentation components can be presented simultaneously or sequentially. FIG. 12 shows an example of a presentation with the exemplary presentation components for an exemplary hospital.

Example 3

Figure 13:
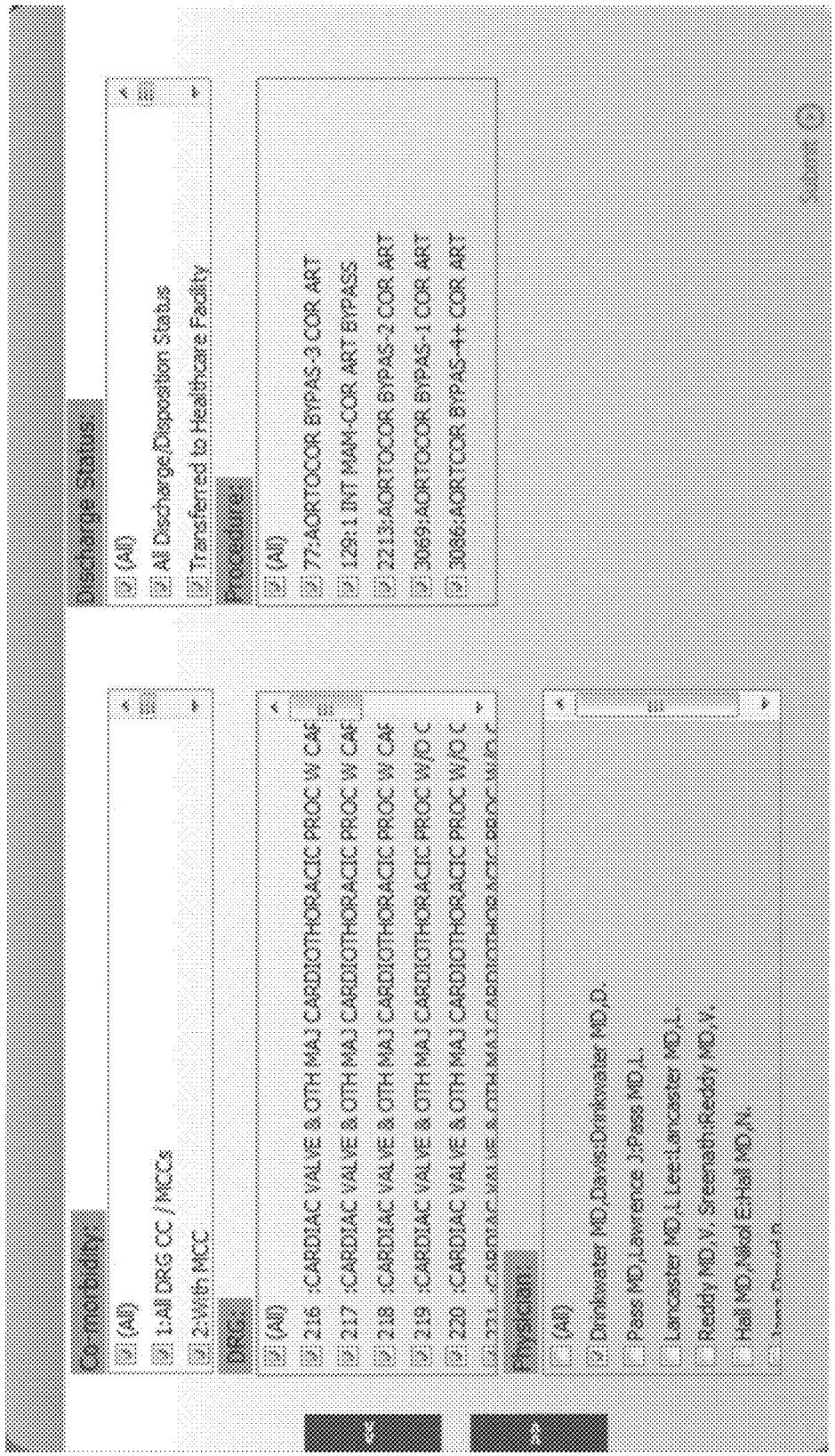
Figure 14:
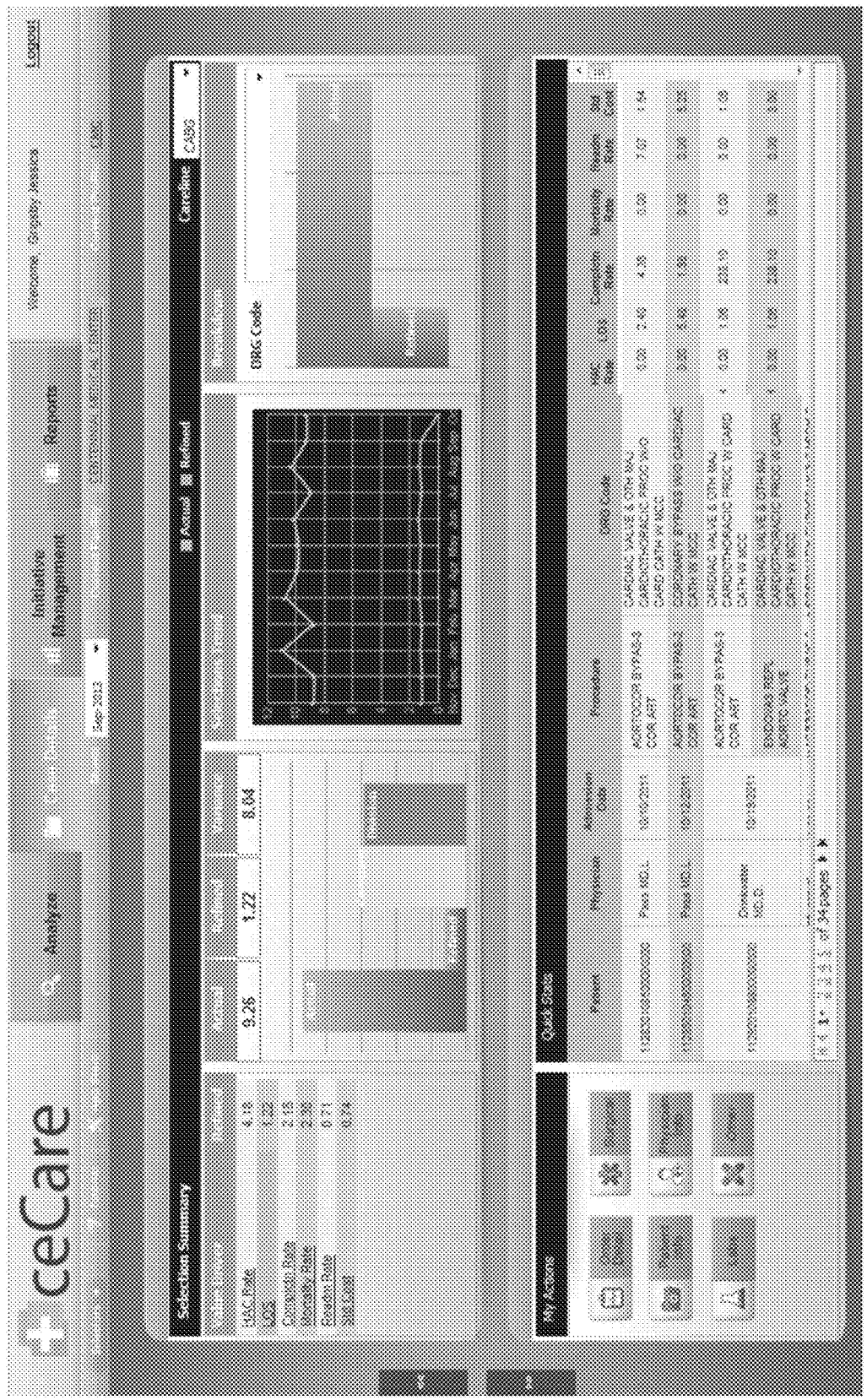
Figure 16:
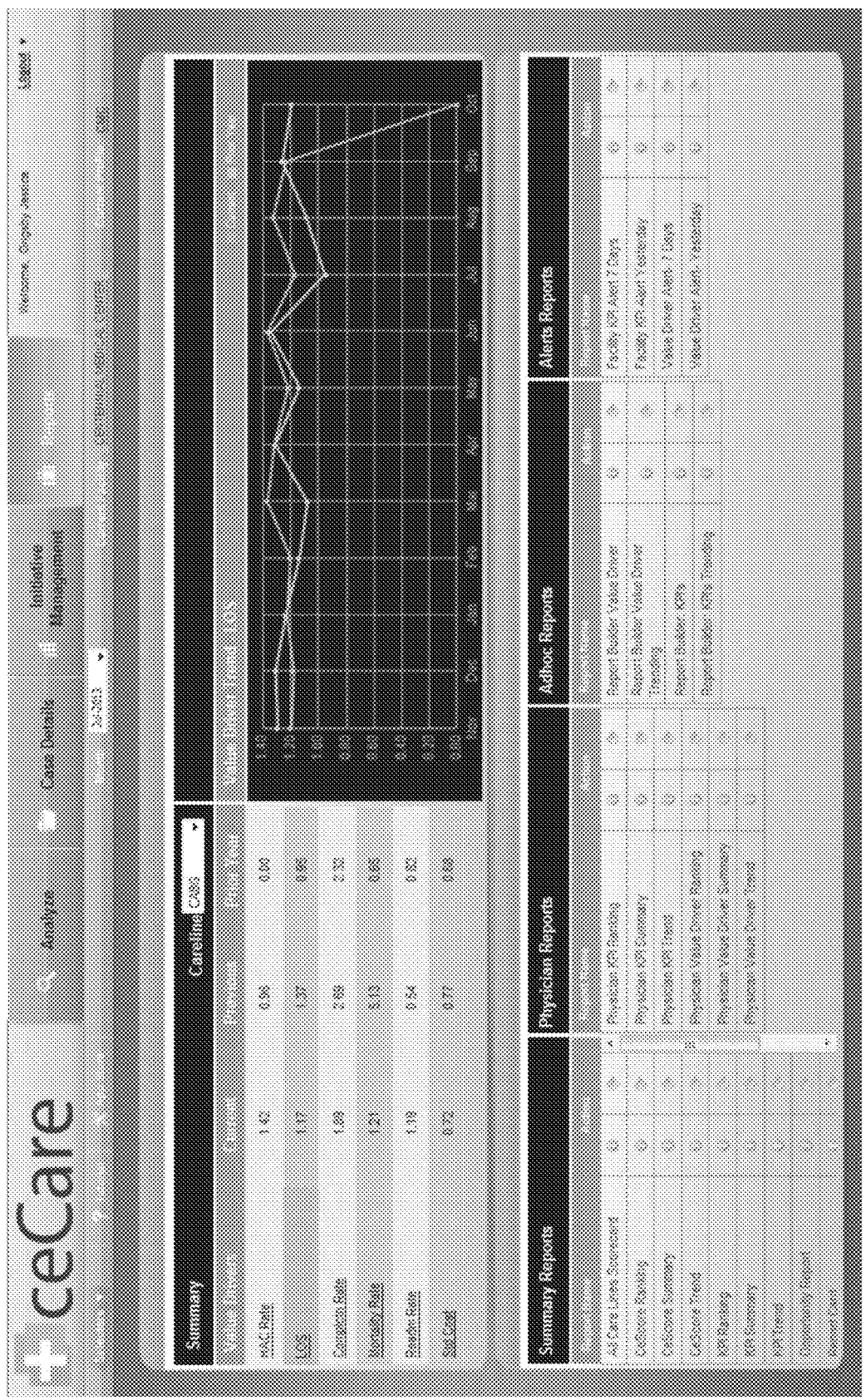

A reviewer can select case parameters of interest using a selection interface, such as one shown in FIG. 13 of interest using a selection interface, such as one shown in FIG. 13. Selections can correspond to selecting or deselecting particular involved entities, procedure types, case statuses, time periods, patient characteristics, etc. Cases corresponding to the selection(s) are identified, and statistics are generated based on the cases. One or more first presentation components show at least some of the generated statistics. A second presentation component shows data pertaining to each of the identified cases. A reviewer can identify one or more cases to exclude for generation of refined statistics. Statistics can then be generated based on remaining cases, and the first presentation component can be updated to further reflect refined statistics. FIG. 14 shows an example of a presentation with the exemplary presentation components for an exemplary hospital.

Example 4

A reviewer can select one or more variables for improvement. In the example shown in FIG. 15, a reviewer selected the CABG care line, a ventilation check-point indicator and a length-of-stay care result. A presentation can auto-populate with various recommendation plans to improve one, more or all of the selected variables. A reviewer can select a template, select an entity at which the recommendation is to be implemented and a month at which it is to begin. The reviewer can set a goal for one or more of the variables and track the entity's progress from a starting point and towards the goals.

Example 5

A presentation (e.g., such as one shown in FIG. 16) can allow a reviewer to view and/or manage various reports pertaining to care assessment. The presentation can list a variety of report names. Clicking on a representation of a report name can cause a presentation to be presented that shows one or more current values associated with the reports, along with historical and/or comparative data. A report can further include an alert history, which can identify data pertaining to various alerts issued within a time period. For example, a report can include data pertaining to all alerts generated in responsive to a satisfaction criterion not being satisfied when evaluated using a value for a care result or check-point indicator. A reviewer can further enter input indicating when a report is to be updated, when a report is to be transmitted or presented, to whom a report is to be transmitted or presented and/or what information is to be presented in a (new or existing) report.

What is claimed is:

1. A care management system for providing presentations to monitor a quality of care being provided to patients, the care management system comprising:
   a case data store that includes a plurality of cases, each case of the plurality of cases identifying:
      a patient;
      a type of a medical care received by the patient, the medical care including a treatment or surgery;
      an entity that provided the medical care;
      a set of check-point indicators, at least one check-point indicator in the set of check-point indicators indicates which medication was provided or when the medication was provided; and
      a care result variable that indicates whether the patient has died, experienced a medical complication, contracted a hospital-acquired condition, was readmitted to a medical institution, or a length of admission at a medical institution;
   an aggregator that, in real-time, identifies a set of recent cases from amongst the plurality of cases, each case of the set of recent cases being associated with a same type of medical care, a same entity and medical care occurring at least partly within a recent time period;
   a population quantifier that:
      analyzes, in real-time, care-result variables in the set of recent cases to determine a real-time population care-result statistic as a function of the recent time period and that relates to a prevalence or magnitude of patient mortality, occurrence of a complication, contraction of a hospital-acquired condition, readmission to an institution, cost of care or length of admission; and
      analyzes, in real-time and for each of the set of check-point indicators, the check-point indicators in the set of recent cases to determine a real-time population check-point statistic as a function of the recent time period, wherein the real-time population check-point statistic determined for each of the at least one check-point indicator corresponds to a quantity of the set of recent cases for which a case-specific satisfaction criterion was satisfied; and
   a satisfaction engine that:
      determines, for each recent case in the set of recent cases mapped to the recent time period and for each of the at least one check-point indicator, whether the case-specific satisfaction criterion is satisfied based on the check-point indicator; and
      identifies a threshold based on a previous time period, the threshold to compare at least one of the real-time population check-point statistics to, the threshold having been generated based on data from case data reflecting medical care occurring during the previous time period;
   a case-specific engine that:
      monitors, in real-time, data pushed and/or pulled from one or more medical devices pertinent to a set of specific cases and, based at least in part on the monitored data, determining that the threshold is satisfied, wherein the one or more medical devices detect a condition of a body of a patient and/or affect the body of the patient, and the data pertains to the detecting and/or the affecting;
      consequent to the determining that the threshold is satisfied, identifies, in real-time, a recommended change to a controllable parameter that influences a check-point pertinent to a specific case of the set of specific cases;
   a presentation engine that:
      consequent to the identifying the recommended change, generates an alert and transmits the alert to a remote user device to alert the remote user device and cause a presentation that includes each of:
         the real-time population care-result statistic;
         an identification of the threshold or whether it is determined that the at least one of the real-time population check-point statistic exceeded the threshold; and
         the real-time population check-point statistic determined for each check-point indicator in the set of check-point indicators;
      updates the presentation in real-time to reflect current values of the real-time population care-result statistic and the real-time population check-point statistics, wherein the presentation or another presentation identifies the controllable parameter and the recommended change to the controllable parameter; and
      consequent to the identifying the recommended change, causes at least one system component to automatically make the recommended change to the controllable parameter.

2. The care management system for providing presentations to monitor a quality of care being provided to patients as recited in claim 1, wherein the presentation is presented at a time less than fifteen minutes from an end of the recent time period.

3. The care management system for providing presentations to monitor a quality of care being provided to patients as recited in claim 1, wherein a subsequent presentation includes the real-time population care-result statistic and the real-time population check-point statistics in a manner that indicates that they pertain to historical data.

4. The care management system for providing presentations to monitor a quality of care being provided to patients as recited in claim 1, wherein the entity is a hospital, physician, nurse or medical team.

5. The care management system for providing presentations to monitor a quality of care being provided to patients as recited in claim 1, wherein the presentation further includes a comparative population care-result statistic corresponding to one or more other entities.

6. The care management system for providing presentations to monitor a quality of care being provided to patients as recited in claim 1, further comprising a case manager that receives an upload that identifies the entity and that includes medical data pertaining to a check-point indicator of the set of check-point indicators and that prior to the identification of the set of recent cases, updates a case in the set of recent cases based on the medical data.

7. A computer-implemented method for providing presentations to monitor a quality of care being provided to patients, the method comprising:
   accessing a case data store that includes a plurality of cases, each case of the plurality of cases identifying:
      a patient;
      a type of a medical care received by the patient, the medical care including a treatment or surgery;
      an entity that provided the medical care;
      a set of check-point indicators, at least one check-point indicator in the set of check-point indicators indicates which medication was provided or when the medication was provided; and a care result variable that indicates whether the patient has died, experienced a medical complication, contracted a hospital-acquired condition, was readmitted to a medical institution, or a length of admission at a medical institution identifying, in real-time, a set of recent cases from amongst the plurality of cases, each case of the set of recent cases being associated with a same type of medical care, a same entity and medical care occurring at least partly within a recent time period;

generating a population care-result statistic corresponding to the recent time period for the set of recent cases based on at least one care-result variable in at least some of the set of recent cases;

analyzing, in real-time, care-result variables in the set of recent cases to determine a real-time population care-result statistic as a function of the recent time period and that relates to a prevalence or magnitude of patient mortality, occurrence of a complication, contraction of a hospital-acquired condition, readmission to an institution, cost of care or length of admission;

determining, for each recent case in the set of recent cases mapped to the recent time period and for each of the at least one check-point indicator, whether a case-specific satisfaction criterion is satisfied based on the check-point indicator;

analyzing, in real-time and for each of the set of check-point indicators, the check-point indicators in the set of recent cases to determine a real-time population check-point statistic as a function of the recent time period, wherein the real-time population check-point statistic determined for each of the at least one check-point indicator corresponds to a quantity of the set of recent cases for which the case-specific satisfaction criterion was satisfied;

identifying a threshold based on a previous time period, the threshold to compare at least one of the real-time population check-point statistics to, the threshold having been generated based on data from case data reflecting medical care occurring during the previous time period;

monitoring, in real-time, data pushed and/or pulled from one or more medical devices pertinent to a set of specific cases and, based at least in part on the monitored data, determining that the threshold is satisfied, wherein the one or more medical devices detect a condition of a body of a patient and/or affect the body of the patient, and the data pertains to the detecting and/or the affecting;

consequent to the determining that the threshold is satisfied, identifying, in real-time, a recommended change to a controllable parameter that influences a check-point pertinent to a specific case of the set of specific cases;

consequent to the identifying the recommended change, generating an alert and transmits the alert to a remote user device to alert the remote user device and cause a presentation that includes:

the real-time population care-result statistic;

an identification of the threshold or whether it is determined that the at least one of the real-time population check-point statistic exceeded the threshold; and the real-time population check-point statistic determined for each check-point indicator in the set of check-point indicators;

updating the presentation in real-time to reflect current values of the real-time population care-result statistic and the real-time population check-point statistic, wherein the presentation or another presentation identifies the controllable parameter and the recommended change to the controllable parameter; and consequent to the identifying the recommended change, causing at least one system component to automatically make the recommended change to the controllable parameter.

8. The method for providing presentations to monitor a quality of care being provided to patients as recited in claim 7, wherein the presentation is presented at a time less than six hours from an end of the recent time period.

9. The method for providing presentations to monitor a quality of care being provided to patients as recited in claim 7, wherein a subsequent presentation includes the real-time population care-result statistic and the real-time population check-point statistics in a manner that indicates that they pertain to historical data.

10. The method for providing presentations to monitor a quality of care being provided to patients as recited in claim 7, wherein the entity is a hospital, physician, nurse or medical team.

11. The method for providing presentations to monitor a quality of care being provided to patients as recited in claim 7, wherein the presentation further includes a comparative population care-result statistic corresponding to one or more other entities.

12. The method for providing presentations to monitor a quality of care being provided to patients as recited in claim 7, further comprising:

receiving an upload that identifies the entity and that includes medical data pertaining to a check-point indicator of the set of check-point indicators; and prior to the identification of the set of recent cases, updating a case in the set of recent cases based on the medical data.

13. A computer-program product tangibly embodied in a non-transitory machine-readable storage medium, including instructions configured to cause one or more data processors to perform actions including:

accessing a case data store that includes a plurality of cases, each case of the plurality of cases identifying:

a patient;

a type of a medical care received by the patient, the medical care including a treatment or surgery;

an entity that provided the medical care;

a set of check-point indicators, at least one check-point indicator in the set of check-point indicators indicates which medication was provided or when the medication was provided; and a care result variable that indicates whether the patient has died, experienced a medical complication, contracted a hospital-acquired condition, was readmitted to a medical institution, or a length of admission at a medical institution identifying, in real-time, a set of recent cases from amongst the plurality of cases, each case of the set of recent cases being associated with a same type of medical care, a same entity and medical care occurring at least partly within a recent time period;

generating a population care-result statistic corresponding to the recent time period for the set of recent cases based on at least one care-result variable in at least some of the set of recent cases;

analyzing, in real-time, care-result variables in the set of recent cases to determine a real-time population care-result statistic as a function of the recent time period and that relates to a prevalence or magnitude of patient mortality, occurrence of a complication, contraction of a hospital-acquired condition, readmission to an institution, cost of care or length of admission;

determining, for each recent case in the set of recent cases mapped to the recent time period and for each of the at least one check-point indicator, whether a case-specific satisfaction criterion is satisfied based on the check-point indicator;

analyzing, in real-time and for each of the set of check-point indicators, the check-point indicators in the set of recent cases to determine a real-time population check-point statistic as a function of the recent time period, wherein the real-time population check-point statistic determined for each of the at least one check-point indicator corresponds to a quantity of the set of recent cases for which the case-specific satisfaction criterion was satisfied;

identifying a threshold based on a previous time period, the threshold to compare at least one of the real-time population check-point statistics to, the threshold having been generated based on data from case data reflecting medical care occurring during the previous time period;

monitoring, in real-time, data pushed and/or pulled from one or more medical devices pertinent to a set of specific cases and, based at least in part on the monitored data, determining that the threshold is satisfied, wherein the one or more medical devices detect a condition of a body of a patient and/or affect the body of the patient, and the data pertains to the detecting and/or the affecting;

consequent to the determining that the threshold is satisfied, identifying, in real-time, a recommended change to a controllable parameter that influences a check-point pertinent to a specific case of the set of specific cases;

consequent to the identifying the recommended change, generates an alert and transmits the alert to a remote user device to alert the remote user device and cause a presentation that includes:
the real-time population care-result statistic;
an identification of the threshold or whether it is determined that the at least one of the real-time population check-point statistic exceeded the threshold; and
the real-time population check-point statistic determined for each check-point indicator in the set of check-point indicators;

updating the presentation in real-time to reflect current values of the real-time population care-result statistic and the real-time population check-point statistic, wherein the presentation or another presentation identifies the controllable parameter and the recommended change to the controllable parameter; and consequent to the identifying the recommended change, causing at least one system component to automatically make the recommended change to the controllable parameter.

14. The computer-program product as recited in claim 13, wherein the presentation is presented at a time less than six hours from an end of the recent time period.

15. The computer-program product as recited in claim 13, wherein a subsequent presentation includes the real-time population care-result statistic and the real-time population check-point statistics in a manner that indicates that they pertain to historical data.

16. The computer-program product as recited in claim 13, wherein the entity is a hospital, physician, nurse or medical team.

17. The computer-program product as recited in claim 13, wherein the presentation further includes a comparative population care-result statistic corresponding to one or more other entities.

18. The care management system for providing presentations to monitor a quality of care being provided to patients as recited in claim 1, wherein:
the population quantifier further analyzes, in real-time, other care-result variables in the set of recent cases to determine an additional real-time care-result statistic relating to another of: a prevalence or magnitude of patient mortality, occurrence of a complication, contraction of a hospital-acquired condition, readmission to an institution, cost of care or length of admission; and
the presentation further includes the additional real-time care-result statistic.

19. The care management system for providing presentations to monitor a quality of care being provided to patients as recited in claim 1, wherein:
the population quantifier further generates a care score based on a combination of the real-time population check-point statistic determined for each check-point indicator in the set of check-point indicators;
the presentation further includes the care score; and
the update of the presentation further reflects a current value of the care score.

20. The method for providing presentations to monitor a quality of care being provided to patients as recited in claim 7, further comprising:
identifying a controllable parameter that influences a check-point in the at least one check-point indicator;
when it is determined that the at least one of the real-time population check-point statistic exceeds the threshold, identifying a recommended change to the controllable parameter;
wherein the presentation or another presentation identifies the controllable parameter and the recommended change to the controllable parameter.

\* \* \* \* \*